(12) United States Patent
Hayakawa et al.

(10) Patent No.: US 10,729,623 B2
(45) Date of Patent: *Aug. 4, 2020

(54) METHOD FOR PRODUCING ELLIPTICAL, NEEDLE-SHAPED, OR ROD-SHAPED POLYMER PARTICLES

(71) Applicant: NISSHINBO HOLDINGS, INC., Tokyo (JP)

(72) Inventors: Kazutoshi Hayakawa, Chiba (JP); Toshifumi Hashiba, Chiba (JP); Erina Matsuzaka, Chiba (JP); Goki Yamada, Chiba (JP)

(73) Assignee: NISSHINBO HOLDINGS, INC., Tokyo (JP)

( * ) Notice: Subject to any disclaimer, the term of this patent is extended or adjusted under 35 U.S.C. 154(b) by 134 days.

This patent is subject to a terminal disclaimer.

(21) Appl. No.: 15/572,196

(22) PCT Filed: May 2, 2016

(86) PCT No.: PCT/JP2016/063545
§ 371 (c)(1),
(2) Date: Nov. 7, 2017

(87) PCT Pub. No.: WO2016/181878
PCT Pub. Date: Nov. 17, 2016

(65) Prior Publication Data
US 2018/0104160 A1    Apr. 19, 2018

(30) Foreign Application Priority Data

May 8, 2015    (JP) .................. 2015-095723

(51) Int. Cl.
| | | |
|---|---|---|
| *A61K 8/02* | (2006.01) | |
| *A61K 8/81* | (2006.01) | |
| *A61Q 1/12* | (2006.01) | |
| *C08F 2/06* | (2006.01) | |
| *C09D 125/04* | (2006.01) | |
| *C08F 112/08* | (2006.01) | |

(Continued)

(52) U.S. Cl.
CPC .............. *A61K 8/02* (2013.01); *A61K 8/0245* (2013.01); *A61K 8/81* (2013.01); *A61K 8/8152* (2013.01); *A61K 8/8158* (2013.01); *A61Q 1/12* (2013.01); *C08F 2/06* (2013.01); *C08F 112/08* (2013.01); *C08F 212/08* (2013.01); *C08F 265/06* (2013.01); *C09D 11/10* (2013.01); *C09D 125/04* (2013.01); *C09D 129/00* (2013.01); *C09D 133/04* (2013.01); *C09D 157/00* (2013.01); *C09J 125/04* (2013.01); *C09J 129/00* (2013.01); *C09J 133/04* (2013.01); *C08F 12/22* (2013.01); *C08F 12/30* (2013.01); *C08F 2500/24* (2013.01)

(58) Field of Classification Search
CPC ................... C08F 212/08; C08F 220/14; C08F 2220/325; C08F 2/20; C08F 2/26; C08F 220/56; C08F 2500/24; C08F 2800/20; C08F 2810/20; C08L 33/12; C08L 2205/025; C09D 129/04; C09D 11/107; C09D 11/108; C09D 125/14; C09D 133/12; A61K 8/0245; A61K 8/8152; A61Q 19/00; A61Q 1/02; C09J 125/14; C09J 133/12; G02B 5/0242

See application file for complete search history.

(56) References Cited

U.S. PATENT DOCUMENTS

2007/0054123 A1    3/2007   Hashiba et al.
2008/0038669 A1    2/2008   Kakino
(Continued)

FOREIGN PATENT DOCUMENTS

| EP | 3296325 A1 | 3/2018 |
|---|---|---|
| JP | 2007-70372 A | 3/2007 |

(Continued)

OTHER PUBLICATIONS

Simovich, et al. (Applied Surface Science, 295 (2014) 203-206) (Year: 2014).*

Heslinga, M. J. et al., "Fabrication of biodegradable spheroidal microparticles for drug delivery applications", Journal of Controlled Release, Elsevier, Sep. 15, 2009, vol. 138, No. 3, pp. 235-242; cited in Extended (supplementary) European Search Report dated Nov. 15, 2018.

Extended (supplementary) European Search Report dated Nov. 15, 2018, issued in counterpart European Application No. 16792603.9. (11 pages).

(Continued)

*Primary Examiner* — Anna R Falkowitz
(74) *Attorney, Agent, or Firm* — Westerman, Hattori, Daniels & Adrian, LLP

(57) ABSTRACT

A method for producing elliptical, needle-shaped, or rod-shaped polymer particles satisfying (1)-(3) below includes a step in which a synthesis solution including water, a mixed solvent of a hydrophilic organic solvent and a hydrophobic organic solvent, a polymeric stabilizer, a polymerization initiator, and an unsaturated monomer is heated, and, at least after the heating has started, the pH of the synthesis solution is adjusted to 5-9 inclusive to perform solution polymerization: (1) the average ($L_{AV}$) length (L) in a two-dimensional projection diagram obtained by irradiating the particles with light from a direction orthogonal to the longitudinal direction is 0.1-80 μm; (2) the average ($D_{AV}$) breadth (D) in the two-dimensional projection diagram obtained by irradiating the particles with light from the direction orthogonal to the longitudinal direction is 0.05-40 μm; and (3) the average ($P_{AV}$) aspect ratio (L/D) calculated from the length (L) and the breadth (D) is 1.5-30.

5 Claims, 2 Drawing Sheets

Figure 1:
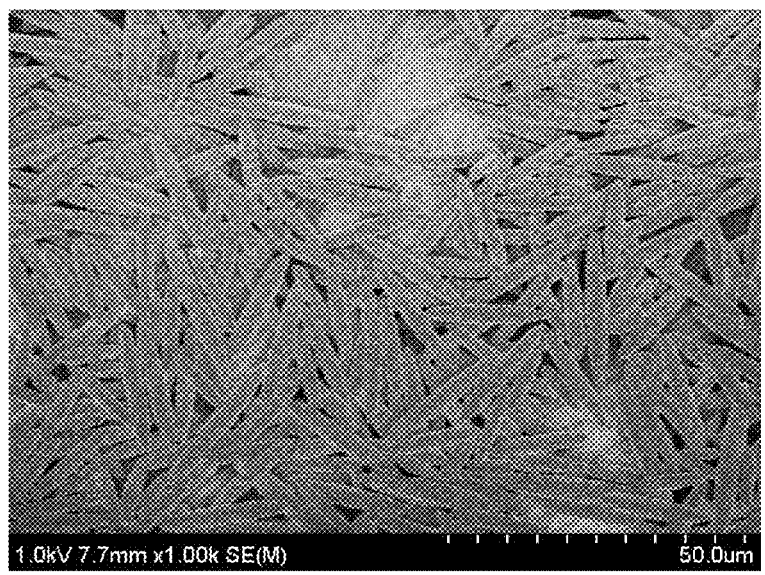

(51) Int. Cl.

| | | |
|---|---|---|
| *C09D 133/04* | (2006.01) | |
| *C09D 11/10* | (2014.01) | |
| *C09J 133/04* | (2006.01) | |
| *C08F 212/08* | (2006.01) | |
| *C08F 265/06* | (2006.01) | |
| *C09D 129/00* | (2006.01) | |
| *C09D 157/00* | (2006.01) | |
| *C09J 125/04* | (2006.01) | |
| *C09J 129/00* | (2006.01) | |
| *C08F 12/22* | (2006.01) | |
| *C08F 12/30* | (2006.01) | |

(56) References Cited

U.S. PATENT DOCUMENTS

| | | |
|---|---|---|
| 2010/0062932 A1 | 3/2010 | Losch et al. |
| 2010/0278884 A1 | 11/2010 | Tanaka et al. |

FOREIGN PATENT DOCUMENTS

| | | | |
|---|---|---|---|
| JP | 2007-326904 A | 12/2007 | |
| JP | 2008-111132 A | 5/2008 | |
| JP | 2009-235353 A | 10/2009 | |
| JP | 2009-235355 | * 10/2009 | ............ C08F 212/08 |
| JP | 2009-235355 A | 10/2009 | |
| JP | 2009-237507 A | 10/2009 | |
| JP | 2010-100689 A | 5/2010 | |
| JP | 2010-518208 A | 5/2010 | |
| JP | 20100689 | * 6/2013 | |
| JP | 2013-131368 A | 7/2013 | |
| JP | 2015-93973 A | 5/2015 | |
| JP | 2016-17048 A | 2/2016 | |

OTHER PUBLICATIONS

International Search Report dated Jul. 12, 2016, issued in counterpart of International Application No. PCT/JP2016/063545 (3 pages).
Simovich, T. et al., "Energy efficient one-pot synthesis of durable superhydrophobic coating through nylon micro-rods", Applied Surface Science, Jan. 15, 2014, vol. 295, pp. 203-206; Cited in Extended (supplementary) European Search Report dated Nov. 15, 2018.
Extended (supplementary) European Search Report dated Nov. 15, 2018, issued in European Application No. 16792601.3. (9 pages).
International Search Report dated Jul. 19, 2016, issued in International Application No. PCT/JP2016/063543, with English translation (5 pages).
Written Opinion dated Jul. 19, 2016, issued in International Application No. PCT/JP2016/063543 (3 pages).
Non-Final Office Action dated May 14, 2019, issued in U.S. Appl. No. 15/571,907 (13 pages).
Non-Final Office Action dated Aug. 16, 2019, issued in U.S. Appl. No. 15/571,907 (13 pages).

* cited by examiner

METHOD FOR PRODUCING ELLIPTICAL, NEEDLE-SHAPED, OR ROD-SHAPED POLYMER PARTICLES

TECHNICAL FIELD

The present invention relates to a method for producing elliptical, needle-shaped or rod-shaped polymer particles.

BACKGROUND ART

Micron-size polymer particles and inorganic particles are used as fillers and specimens in a variety of fields, such as electrical and electronic materials, optical materials, paints, inks, construction materials, biological and pharmaceutical materials, and cosmetics. In recent years, active research has been carried out particularly on particles of unusual, non-spherical shapes. Because such particles confer diverse properties, including optical characteristics and tactile feel, new applications are constantly being developed.

The inventors have been working on the development of elliptical or needle-shaped polymer particles of high aspect ratio, and have discovered particles with characteristics superior to those of conventional spherical particles in terms of such properties as hiding power, light-diffusing ability and tactile qualities (Patent Documents 1 and 2).

However, although elliptical or needle-shaped polymer particles do have excellent characteristics owing to their shape, control of the shape and particle size tends to lead to an increase in impurities and agglomerates, which sometimes complicates filtration and classification and is thus a major problem.

In light of such circumstances, from an industrial standpoint, there has existed a desire for a method of producing polymer particles which is able to precisely and stably obtain such shapes.

PRIOR ART DOCUMENTS

Patent Documents

Patent Document 1: JP-A 2009-235353
Patent Document 2: JP-A 2009-235355

SUMMARY OF THE INVENTION

Problems to be Solved by the Invention

It is therefore an object of the present invention to provide a method for producing elliptical, needle-shaped or rod-shaped polymer particles which can, from an industrial standpoint, precisely and stably obtain elliptical, needle-shaped or rod-shaped polymer particles having an excellent monodispersibility and few impurities and agglomerates.

Means for Solving the Problems

The inventors have conducted extensive investigations aimed at achieving the above objects. As a result, they have discovered that by carrying out solution polymerization which involves heating a synthesis solution containing a mixed solvent of water, a hydrophilic organic solvent and a hydrophobic organic solvent, a high-molecular-weight stabilizer, a polymerization initiator and an unsaturated monomer; and, at least after the start of heating, adjusting the pH of the synthesis solution to 5 or less or to 9 or more, monodispersible elliptical, needle-shaped or rod-shaped polymer particles with few agglomerates or impurities can be obtained while retaining the elliptical, needle-like or rod-like shape.

Accordingly, the invention provides the following method for producing elliptical, needle-shaped or rod-shaped polymer particles.

1. A method for producing elliptical, needle-shaped or rod-shaped polymer particles which satisfy conditions (1) to (3) below:
   (1) a two-dimensional projection obtained by irradiating the particle with light from a direction orthogonal to a long axis of the particle has a length L with an average value $L_{AV}$ of from 0.1 to 80 μm,
   (2) a two-dimensional projection obtained by irradiating the particle with light from a direction orthogonal to a long axis of the particle has a breadth D with an average value $D_{AV}$ of from 0.05 to 40 μm, and
   (3) the aspect ratio L/D calculated from the length L and breadth D has an average value $P_{AV}$ of from 1.5 to 30,
   the method comprising the step of carrying out solution polymerization by heating a synthesis solution containing a mixed solvent of water, a hydrophilic organic solvent and a hydrophobic organic solvent, a high-molecular-weight stabilizer, a polymerization initiator and an unsaturated monomer and, at least after the start of heating, adjusting the pH of the synthesis solution to 5 or less or to 9 or more.
2. The method for producing elliptical, needle-shaped or rod-shaped polymer particles of 1 above, wherein the mixing ratio of the water, hydrophilic organic solvent and hydrophobic organic solvent, expressed as a weight ratio, is from 99:0.5:0.5 to 25:55:20.
3. The method for producing elliptical, needle-shaped or rod-shaped polymer particles of 1 or 2 above, wherein the hydrophobic organic solvent is a high-molecular-weight compound having a molecular weight of at least 200.
4. The method for producing elliptical, needle-shaped or rod-shaped polymer particles of any of 1 to 3 above, wherein the unsaturated monomer includes at least one monomer selected from the group consisting of styrenic monomers, (meth)acrylic ester monomers, vinyl carboxylate monomers and polyfunctional unsaturated monomers.
5. The method for producing elliptical, needle-shaped or rod-shaped polymer particles of any of 1 to 4 above, wherein the unsaturated monomer contains at least one reactive functional group selected from epoxy, hydroxyl, carboxyl, amino, amide and thiol groups.
6. The method for producing elliptical, needle-shaped or rod-shaped polymer particles of 5 above, further comprising, after the solution polymerization step, the step of crosslinking the resulting elliptical, needle-shaped or rod-shaped polymer particles with an organic compound having a reactive group that reacts with the reactive functional group by reacting functional groups included in the elliptical, needle-shaped or rod-shaped polymer particles with reactive groups included in the organic compound in the presence of a solvent that dissolves the organic compound but does not dissolve the elliptical, needle-shaped or rod-shaped polymer particles.
7. The method for producing elliptical, needle-shaped or rod-shaped polymer particles of 6 above, wherein the organic compound includes at least one functional group selected from hydroxyl, carboxyl, amino, thiol, carbonyl, ether, cyano, epoxy, amide, isocyanate, carbodiimide and oxazoline groups.
8. An elliptical, needle-shaped or rod-shaped polymer particle obtained by the production method of any of 1 to 7 above.

9. A dispersion or resin composition obtained using the elliptical, needle-shaped or rod-shaped polymer particle of 8 above.
10. A light-diffusing plate or light-diffusing sheet obtained using the elliptical, needle-shaped or rod-shaped polymer particle of 8 above.
11. A paint composition obtained using the elliptical, needle-shaped or rod-shaped polymer particle of 8 above.
12. An ink composition obtained using the elliptical, needle-shaped or rod-shaped polymer particle of 8 above.
13. A cosmetic preparation obtained using the elliptical, needle-shaped or rod-shaped polymer particle of 8 above.
14. A material for the electrical or electronics industry obtained using the elliptical, needle-shaped or rod-shaped polymer particle of 8 above.
15. An adhesive obtained using the elliptical, needle-shaped or rod-shaped polymer particle of 8 above.
16. A thermally cavitated product having pores obtained using the elliptical, needle-shaped or rod-shaped polymer particle of 8 above.
17. A diagnostic agent for medical use obtained using the elliptical, needle-shaped or rod-shaped polymer particle of 8 above.

Advantageous Effects of the Invention

The method for producing elliptical, needle-shaped or rod-shaped polymer particles of the invention makes it possible to efficiently produce monodispersible elliptical, needle-shaped or rod-shaped polymer particles having few agglomerates or impurities.

BRIEF DESCRIPTION OF THE DIAGRAMS

Figure 2:
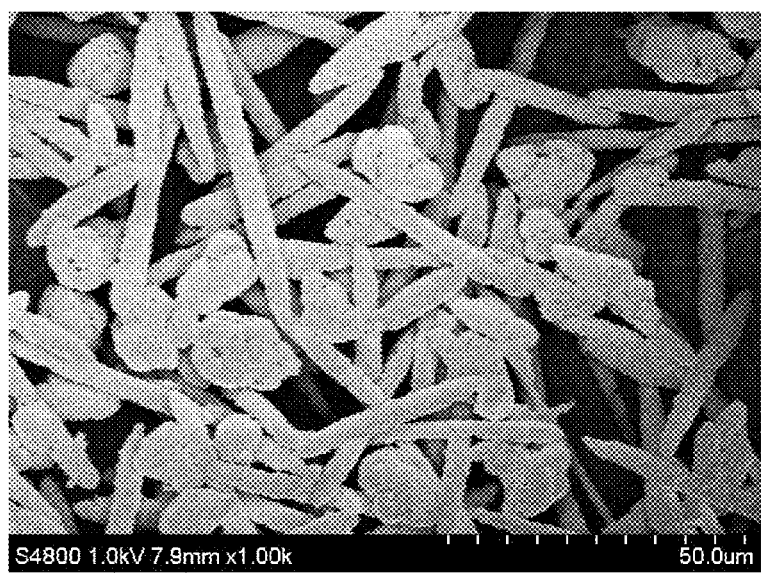
Figure 3:
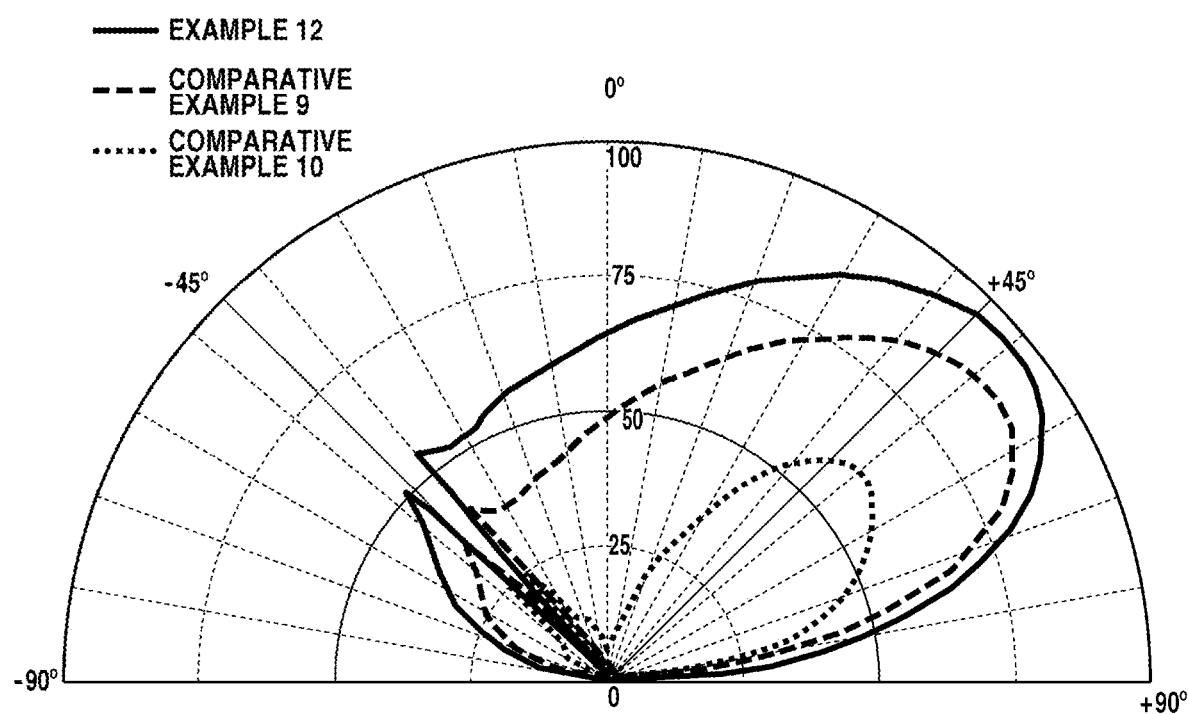

FIG. 1 shows a scanning electron micrograph of particles obtained in Working Example 1.
FIG. 2 shows a scanning electron micrograph of particles obtained in Comparative Example 1.
FIG. 3 is a diagram showing the light scattering distribution of reflected light obtained using an automated goniophotometer in test sheets prepared in Working Example 12 and Comparative Examples 9 and 10.

EMBODIMENT FOR CARRYING OUT THE INVENTION

[Method for Producing Elliptical, Needle-Shaped or Rod-Shaped Polymer Particles]
[Solution Polymerization Step]

The inventive method for producing elliptical, needle-shaped or rod-shaped polymer particles is a method for producing elliptical, needle-shaped or rod-shaped polymer particles which satisfy conditions (1) to (3) below:
(1) a two-dimensional projection obtained by irradiating the particle with light from a direction orthogonal to a long axis of the particle has a length L with an average value $L_{AV}$ of from 0.1 to 80 μm,
(2) a two-dimensional projection obtained by irradiating the particle with light from a direction orthogonal to a long axis of the particle has a breadth D with an average value $D_{AV}$ of from 0.05 to 40 μm, and
(3) the aspect ratio L/D calculated from the length L and breadth D has an average value $P_{AV}$ of from 1.5 to 30,
which method includes the step of carrying out solution polymerization by heating a synthesis solution containing a mixed solvent of water, a hydrophilic organic solvent and a hydrophobic organic solvent, a high-molecular-weight stabilizer, a polymerization initiator and an unsaturated monomer and, at least after the start of heating, adjusting the pH of the synthesis solution to 5 or less or to 9 or more.

Specific examples of solution polymerization methods include suspension polymerization, emulsion polymerization, dispersion polymerization and seed polymerization methods, as well as combined methods based on these.

Suspension polymerization is a process in which a monomer and agents such as a polymerization initiator that are soluble in the monomer are mechanically agitated in a medium in which these do not readily dissolve, causing the polymerization reaction to proceed in a suspended state and causing polymer particles to separate out or form.

Emulsion polymerization is a process in which a medium such as water is mixed with a monomer and agents such as an emulsifying agent (surfactant) that are poorly soluble in the medium, along with which a polymerization initiator soluble in the medium is added, causing the polymerization reaction to proceed and polymer particles to separate out or form.

Dispersion polymerization is a process in which the polymerization reaction is made to proceed in a uniform solution of monomer, initiator, dispersion stabilizer and the like dissolved in a liquid medium within which the monomer dissolves but becomes insoluble with polymerization, causing polymer particles to separate out or form.

Seed polymerization is a polymerization process in which other particles serving as seeds are added beforehand at the time of polymerization and the polymerization reactions are carried out at the surface of these particles.

The elliptical, needle-shaped or rod-shaped polymer particle of the invention can be obtained by these various types of solution polymerization, although a process based on suspension polymerization, emulsion polymerization, dispersion polymerization or a combination thereof is more preferred. With these methods, the seed particle preparation step required in seed polymerization can be omitted.

Adjustment of the pH is carried out at least following the start of heating, although it may be carried out before the start of heating. After adjusting the pH of the synthesis solution to 5 or less or to 9 or more, it is preferable to maintain the pH at 5 or less or at 9 or more until completion of the reaction.

The synthesis solution has a pH of preferably from 0 to 5 or from 9 to 14, more preferably from 0 to 4 or from 10 to 14, even more preferably from 0 to 3 or from 11 to 14, and most preferably from 0 to 2 or from 12 to 14. By thus shifting the pH to the acidic or alkaline side, radical polymerization proceeds stably, resulting in the formation of elliptical, needle-shaped or rod-shaped polymer particles. Also, the distinctive shape attributes, including size and aspect ratio, are more easily controlled, as a result of which the level of agglomerates or impurities such as mutually sticking particles decreases, enabling the particles to be stably obtained. When the reaction is made to proceed with the pH shifted to the acidic side, the polymerization reaction proceeds more stably; hence, it is preferable for the pH to be from 0 to 5.

Adjustment of the pH may be carried out by, for example, the gradual dropwise addition of a pH adjustor to the synthesis solution following the start of heating so as to shift the pH to the acidic or alkaline side. Alternatively, when the subsequently described persulfate is used as the polymerization initiator, because it breaks down during the polymerization reaction and forms an acid, the pH gradually decreases. In this case, a pH adjustor need not be added.

Examples of suitable pH adjustors include acids such as citric acid, tartaric acid, lactic acid, glycolic acid, hydrochloric acid, nitric acid, sodium citrate, sodium lactate, succinic acid, acetic acid, sodium acetate, fumaric acid, sulfuric acid, malic acid and phosphoric acid; and alkalis such as sodium hydroxide, potassium hydroxide, calcium hydroxide, magnesium hydroxide, sodium carbonate, potassium carbonate, calcium carbonate, ammonium carbonate, ammonia, morpholine, triethanolamine, diethanolamine, dimethylamine, diethylamine, trimethylamine and triethylamine.

By adjusting the pH of the synthesis solution to 5 or less or to 9 or more and carrying out solution polymerization, growth at the particle interior or surface layer proceeds while the target elliptically shaped particle skeleton is being formed, and so monodispersed elliptical, needle-shaped or rod-shaped polymer particles can be stably obtained with little agglomerates or impurities.

In this invention, the synthesis solution pH can be determined by using a pH meter or pH test paper to measure the pH of the synthesis solution in an agitated state.

The unsaturated monomer used in the inventive method for producing elliptical, needle-shaped or rod-shaped polymer particles is not particularly limited. Preferred unsaturated monomers are exemplified by styrenic monomers, (meth)acrylic ester monomers, vinyl carboxylate monomers, N-vinyl compound monomers, olefinic monomers, fluorinated olefinic monomers, conjugated diene monomers, ionic functional group-containing monomers and polyfunctional unsaturated monomers (these are collectively referred to below as "Unsaturated Monomer A"). These may be used singly or two or more may be used in combination.

Examples of the styrenic monomers include styrene, o-methylstyrene, n-methylstyrene, p-methylstyrene, c-methylstyrene, o-ethylstyrene, methylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene and 3,4-dichlorostyrene.

Examples of the (meth)acrylic ester monomers include hydrocarbon group-containing (meth)acrylic monomers such as methyl (meth)acrylate, ethyl (meth)acrylate, propyl (meth)acrylate, n-butyl (meth)acrylate, isobutyl (meth)acrylate, pentyl (meth)acrylate, hexyl (meth)acrylate, 2-ethylhexyl (meth)acrylate, octyl (meth)acrylate, nonyl (meth)acrylate, decyl (meth)acrylate, dodecyl (meth)acrylate, lauryl (meth)acrylate, stearyl (meth)acrylate, cyclohexyl (meth)acrylate, isobornyl (meth)acrylate, phenyl (meth)acrylate, toluyl (meth)acrylate and benzyl (meth)acrylate; fluorine-containing (meth)acrylic monomers such as 2,2,2-trifluoroethyl (meth)acrylate, 3,3,3-trifluoropropyl (meth)acrylate, 2-(perfluoroethyl)ethyl (meth)acrylate, 2-perfluoroethyl-2-perfluorobutylethyl (meth)acrylate, 2-perfluoroethyl (meth)acrylate, tetrafluoropropyl (meth)acrylate, perfluoromethyl (meth)acrylate, 1,1,1,3,3,3-hexafluoropropan-2-yl (meth)acrylate, 2-perfluoromethyl-2-perfluoroethylmethyl (meth)acrylate, 2-(perfluorohexyl)ethyl (meth)acrylate, 2-(perfluorodecyl)ethyl (meth)acrylate and 2-(perfluorohexadecyl)ethyl (meth)acrylate; alkylamino group-containing (meth)acrylic monomers such as N-propylaminoethyl acrylate, N-ethylaminopropyl (meth)acrylate, N-phenylaminoethyl (meth)acrylate and N-cyclohexylaminoethyl (meth)acrylate; silicon-containing (meth)acrylic monomers such as γ-(methacryloyloxypropyl) trimethoxysilane and γ-(methacryloyloxypropyl) dimethoxymethylsilane; alkoxy group-containing (meth) acrylic monomers such as (poly)ethylene glycol mono (meth)acrylate, 2-methoxyethyl (meth)acrylate and 3-methoxybutyl (meth)acrylate; (poly)alkylene glycol (meth)acrylic monomers such as (poly)propylene glycol mono(meth)acrylate; alkoxy(poly)alkylene glycol (meth) acrylic monomers such as methoxy(poly)ethylene glycol mono(meth)acrylate and methoxy(poly)propylene glycol mono(meth)acrylate; and 2-chloroethyl (meth)acrylate and methyl α-chloro(meth)acrylate.

Examples of the vinyl carboxylate monomers include vinyl acetate, vinyl propionate, vinyl benzoate, vinyl butyrate, vinyl formate, vinyl valerate and vinyl pivalate.

Examples of the N-vinyl compound monomers include N-vinylpyrrole, N-vinylcarbazole, N-vinylindole and N-vinylpyrrolidone.

Examples of the olefinic monomers include ethylene and propylene. Examples of the fluorinated olefinic monomers include vinyl fluoride, vinylidene fluoride, tetrafluoroethylene and hexafluoropropylene. Examples of the conjugated diene monomers include butadiene and isoprene.

Examples of the ionic functional group-containing monomers include those containing an anionic functional group such as a sulfonic acid group, phosphoric acid group or phenolic hydroxyl group (e.g., sodium p-styrenesulfonate) or a cationic functional group such as an amino, imidazole, pyridine or amidino group. A specific example is sodium p-styrenesulfonate.

Examples of the polyfunctional unsaturated monomers include aromatic divinyl compounds such as divinylbenzene, divinylbiphenyl and divinylnaphthalene; (poly)alkylene glycol di(meth)acrylates such as (poly)ethylene glycol di(meth)acrylate, (poly)propylene glycol di(meth)acrylate and (poly)tetramethylene glycol di(meth)acrylate; alkanediol di(meth)acrylates such as 1,6-hexanediol di(meth)acrylate, 1,8-octanediol di(meth)acrylate, 1,9-nonanediol di(meth)acrylate, 1,10-decanediol di(meth)acrylate, 1,12-dodecanediol di(meth)acrylate, 3-methyl-1,5-pentanediol di(meth)acrylate, 2,4-diethyl-1,5-pentanediol di(meth)acrylate, butylethylpropanediol di(meth)acrylate, 3-methyl-1,7-octanediol di(meth)acrylate and 2-methyl-1,8-octanediol di(meth)acrylate; alkanediol di(meth)acrylates such as 1,6-hexanediol di(meth)acrylate, 1,8-octanediol di(meth)acrylate, 1,9-nonanediol di(meth)acrylate, 1,10-decanediol di(meth)acrylate, 1,12-dodecanediol di(meth)acrylate, 3-methyl-1,5-pentanediol di(meth)acrylate, 2,4-diethyl-1,5-pentanediol di(meth)acrylate, butylethylpropanediol di(meth)acrylate, 3-methyl-1,7-octanediol di(meth)acrylate and 2-methyl-1,8-octanediol di(meth)acrylate; polyfunctional (meth)acrylates such as glycerol di(meth)acrylate, pentaerythritol tri(meth)acrylate, pentaerythritol tetra(meth)acrylate, pentaerythritol di(meth)acrylate, pentaerythritol tetra(meth)acrylate, glycerol acryloxy di(meth)acrylate, ethoxylated cyclohexane dimethanol di(meth)acrylate, ethoxylated bisphenol A di(meth)acrylate, tricyclodecane dimethanol di(meth)acrylate, propoxylated ethoxylated bisphenol A di(meth)acrylate, 1,1,1-trishydroxymethylethane di(meth)acrylate, 1,1,1-trishydroxymethylethane tri(meth) acrylate, 1,1,1-trishydroxymethylpropane tri(meth)acrylate, caprolactone-modified dipentaerythritol hexa(meth)acrylate, caprolactone-modified hydroxypivalate neopentyl glycol di(meth)acrylate, polyester (meth)acrylate and urethane (meth)acrylate; and compounds such as N,N-divinylaniline, divinyl ether, divinylsulfide and divinylsulfone. These may be used singly or two or more may be used in combination.

Of these, styrenic monomers, (meth)acrylic ester monomers, vinyl carboxylate monomers and polyfunctional unsaturated monomers are preferred. By using these, elliptical, needle-shaped or rod-shaped polymer particles having the above-described shapes can be easily and inexpensively obtained.

In the inventive method for producing elliptical, needle-shaped or rod-shaped polymer particles, use can additionally be made of, as monomers other than Unsaturated Monomer A, unsaturated monomers containing a reactive functional group such as a hydrophilic functional group or an active hydrogen group (which reactive functional group-containing unsaturated monomers are referred to below as "Unsaturated Monomer B"). The use of Unsaturated Monomer B is essential particularly when carrying out the subsequently described crosslinking step.

Examples of the reactive functional group include epoxy, carboxyl, amide, hydroxyl, amino, alkylene oxide, thiol, carbonyl, ether, cyano, isocyanate, carbodiimide and oxazoline groups. Of these, epoxy, carboxyl, amide, hydroxyl, amino and thiol groups are preferred.

The reactive functional group-containing Unsaturated Monomer B is exemplified as shown below. In the explanation that follows, "$C_n$" means "n number of carbon atoms."

(1) Epoxy Group-Containing Unsaturated Monomers

Examples include epoxy group-containing (meth)acrylates such as glycidyl (meth)acrylate, (β-methyl)glycidyl (meth)acrylate, 3,4-epoxycyclohexyl (meth)acrylate, glycidyl α-ethylacrylate, glycidyl α-n-propylacrylate, glycidyl α-n-butylacrylate, 3,4-epoxybutyl acrylate, 3,4-epoxybutyl methacrylate, 4,5-epoxypentyl methacrylate, 6,7-epoxyheptyl acrylate, 6,7-epoxyheptyl methacrylate and 6,7-epoxyheptyl α-ethylacrylate; vinyl glycidyl ethers such as o-vinylphenyl glycidyl ether, m-vinylphenyl glycidyl ether, p-vinylphenyl glycidyl ether, o-vinylbenzyl glycidyl ether, m-vinylbenzyl glycidyl ether and p-vinylbenzyl glycidyl ether; and monomers having an ethylenically unsaturated bond and an epoxy group, such as 2,3-diglycidyloxystyrene, 3,4-diglycidyloxystyrene, 2,4-diglycidyloxystyrene, 3,5-diglycidyloxystyrene, 2,6-diglycidyloxystyrene, 5-vinylpyrogallol triglycidyl ether, 4-vinylpyrogallol triglycidyl ether, vinylfluoroglycinol triglycidyl ether, 2,3-dihydroxymethylstyrene diglycidyl ether, 3,4-dihydroxymethylstyrene diglycidyl ether, 2,4-dihydroxymethylstyrene diglycidyl ether, 3,5-dihydroxymethylstyrene diglycidyl ether, 2,6-dihydroxymethylstyrene diglycidyl ether, 2,3,4-trihydroxymethylstyrene triglycidyl ether, 1,3,5-trihydroxymethylstyrene triglycidyl ether, allyl glycidyl ether, 3,4-epoxyvinylcyclohexane, di(β-methyl)glycidyl maleate and di(β-methyl)glycidyl fumarate.

(2) Carboxyl Group-Containing Unsaturated Monomers

Examples include unsaturated carboxylic acids such as acrylic acid, methacrylic acid, crotonic acid, cinnamic acid, itaconic acid, maleic acid and fumaric acid; mono($C_{1-8}$ alkyl) esters of itaconic acid such as monobutyl itaconate; mono($C_{1-8}$ alkyl) esters of maleic acid such as monobutyl maleate; vinyl group-containing aromatic carboxylic acids such as vinylbenzoic acid; and salts thereof.

(3) Amide Group-Containing Unsaturated Monomers

Examples include (meth)acrylamide, c-ethyl (meth)acrylamide, N-methyl (meth)acrylamide, N-butoxymethyl (meth)acrylamide, diacetone (meth)acrylamide, N,N-dimethyl (meth)acrylamide, N,N-diethyl (meth)acrylamide, N,N-dimethyl-p-styrene sulfonamide, N,N-dimethylaminoethyl (meth)acrylamide, N,N-diethylaminoethyl (meth)acrylamide, N,N-dimethylaminopropyl (meth)acrylamide and N,N-diethylaminopropyl (meth)acrylamide.

(4) Hydroxyl Group-Containing Unsaturated Monomers

Examples include hydroxyl group-containing (meth) acrylic monomers such as 2-hydroxyethyl (meth)acrylate, 2-hydroxypropyl (meth)acrylate, 3-hydroxypropyl (meth) acrylate and 4-hydroxybutyl (meth)acrylate; polyalkylene glycol (meth)acrylic monomers such as polyethylene glycol mono(meth)acrylate and polypropylene glycol mono(meth) acrylate; hydroxyalkyl vinyl ether monomers such as hydroxyethyl vinyl ether and hydroxybutyl vinyl ether; and hydroxyl group-containing allyl monomers such as allyl alcohol and 2-hydroxyethyl allyl ether.

(5) Amino Group-Containing Unsaturated Monomers

Examples include allylamine monomers such as allylamine and N-methylallylamine; amino group-containing styrenic monomers such as p-aminostyrene; amino group-containing acrylic monomers such as 2-aminoethyl (meth) acrylate and 2-(dimethylamino)ethyl methacrylate; and triazine-containing monomers such as 2-vinyl-4,6-diamino-S-triazine. Of these, compounds having a primary or secondary amino group are preferred.

(6) Thiol (Mercapto) Group-Containing Unsaturated Monomers

Examples include mercapto group-containing (meth) acrylic monomers such as N-(2-mercaptoethyl) acrylamide, N-(2-mercapto-1-carboxyethyl) acrylamide, N-(2-mercaptoethyl) methacrylamide, N-(4-mercaptophenyl) acrylamide, N-(7-mercaptonaphthyl) acrylamide, maleic acid mono (2-mercaptoethylamide), 2-mercaptoethyl (meth)acrylate and 2-mercapto-1-carboxyethyl (meth)acrylate.

(7) Carbonyl Group-Containing Unsaturated Monomers

Examples include vinyl group-containing ketones such as vinyl methyl ketone, vinyl hexyl ketone and methyl isopropenyl ketone.

(8) Ether Group-Containing Unsaturated Monomers

Examples include vinyl group-containing ether monomers such as vinyl methyl ether, vinyl ethyl ether and vinyl isobutyl ether.

(9) Cyano Group-Containing Unsaturated Monomers

Examples include acrylonitrile, methacrylonitrile, hexenenitrile, 4-pentenenitrile and p-cyanostyrene.

Unsaturated Monomer B may be a monomer that includes one of the above reactive functional groups or may be a monomer that includes two or more such reactive functional groups. Unsaturated Monomer B may be of one type used alone, or two or more types may be used in combination.

Of the above, preferred examples of Unsaturated Monomer B include glycidyl (meth)acrylate, (meth)acrylic acid, (meth)acrylamide, N-methyl (meth)acrylamide, N,N-dimethyl (meth)acrylamide, N,N-diethyl (meth)acrylamide, hydroxyalkyl (meth)acrylates such as 2-hydroxyethyl (meth)acrylate and 3-hydroxypropyl (meth)acrylate, polyalkylene glycol (meth)acrylates such as polyethylene glycol (meth)acrylate and polypropylene (glycol (meth)acrylate, p-aminostyrene and 2-aminoethyl (meth)acrylate.

Unsaturated Monomers A and B may each be used independently, or Unsaturated Monomers A and B may be used in a suitable combination. When Unsaturated Monomers A and B are used in combination, they are used in relative amounts, expressed in terms of the molar ratio A:B, of preferably from 99:1 to 1:99. To take full advantage of the characteristics of the reactive functional groups, the molar ratio is more preferably from 95:5 to 5:95, even more preferably from 85:15 to 15:85, and most preferably from 80:20 to 20:80. By setting the amounts in which the respective monomers are used within this range, the subsequently described crosslinked particles or particles with a high reactivity for obtaining a bonded resin layer as the particle surface layer can be easily obtained.

A mixed solvent of water, a hydrophilic organic solvent and a hydrophobic organic solvent is used as the solvent for synthesis. These solvents should be suitable ones selected from among ordinary solvents according to, for example, the starting materials to be used. In this invention, "hydrophilic organic solvent" refers to a solvent which maintains a uniform appearance as a mixed solvent with water. Also, "hydrophobic organic solvent" refers to a solvent which, when gently mixed with an equal volume of pure water at one atmosphere ($1.013 \times 10^5$ Pa) and a temperature of 20° C., results in a mixed liquid that cannot maintain a uniform appearance after flow has subsided.

Examples of solvents that may be used include water, deionized water and distilled water; and hydrophilic organic solvents such as methanol, ethanol, 1-propanol, 2-propanol, ethylene glycol, propylene glycol, butylene glycol, dipropylene glycol, methyl cellosolve, ethyl cellosolve, propyl cellosolve, methyl cellosolve acetate, ethyl cellosolve acetate, methyl carbitol, ethyl carbitol, butyl carbitol, ethyl carbitol acetate, acetone, tetrahydrofuran, dimethyl formamide, N-methyl-2-pyrrolidone and acetonitrile. These may be used singly or two or more may be used in admixture.

Examples of hydrophobic organic solvents include higher alcohols such as 1-butanol, 2-butanol, isobutanol, t-butanol, 1-pentanol, 2-pentanol, 3-pentanol, 2-methyl-1-butanol, iso-pentyl alcohol, t-pentyl alcohol, 1-hexanol, 2-methyl-1-pentanol, 4-methyl-2-pentanol, 2-ethylbutanol, 1-heptanol, 2-heptanol, 3-heptanol, 2-octanol, 2-ethyl-1-hexanol, benzyl alcohol and cyclohexanol; ether alcohols such as butyl cellosolve; polyethers such as polypropylene glycol and polybutylene glycol; ketones such as methyl ethyl ketone, methyl isobutyl ketone and cyclohexanone; esters such as ethyl acetate, butyl acetate, ethyl propionate and butyl carbitol acetate; aliphatic or aromatic hydrocarbons such as pentane, 2-methylbutane, n-hexane, cyclohexane, 2-methylpentane, 2,2-dimethylbutane, 2,3-dimethylbutane, heptane, n-octane, isooctane, 2,2,3-trimethylpentane, decane, nonane, cyclopentane, methyl cyclopentane, methyl cyclohexane, ethyl cyclohexane, p-menthane, dicyclohexyl, benzene, toluene, xylene, ethylbenzene, liquid paraffin, mineral oil and heat transfer medium oils; siloxane compounds such as polydimethylsiloxane, polymethylphenylsiloxane, polydiphenylsiloxane and silicone oils; and halogenated hydrocarbons such as carbon tetrachloride, trichloroethylene, chlorobenzene and tetrabromoethane. These hydrophobic organic solvents may include modified compounds and copolymers and other modified polymer compounds that are substituted with carbon, nitrogen, oxygen, hydrogen, halogen or the like, within a range that does detract from the advantageous effects of the invention. Such hydrophobic organic solvents may be used singly or two or more may be used in combination.

Of the above hydrophobic organic solvents, the use of a hydrophobic organic solvent which has 8 or more carbon atoms and does not react with the starting unsaturated monomer under the polymerization conditions is preferred. By having such a hydrophobic organic solvent be present within the reaction system, the dispersibility of the elliptical, needle-shaped or rod-shaped polymer particles as they form can be enhanced, making more uniform control of the particle size possible.

This organic compound having 8 or more carbon atoms is not particularly limited, so long as it is a liquid—at least at the temperature at which the polymerization is made to proceed, and does not have an adverse influence on cross-linked polymer particle formation. However it is desirable to use an organic compound having a melting point of not above 80° C., preferably not above 60° C., more preferably not above 40° C., and still more preferably not above 30° C. Examples of such organic compounds include aliphatic or aromatic hydrocarbons such as n-octane, isooctane, 2,2,3-trimethylpentane, decane, nonane, cyclopentane, methylcyclopentane, methylcyclohexane, ethylcyclohexane, p-menthane, dicyclohexyl, benzene, toluene, xylene, ethylbenzene, liquid paraffin, mineral oil and heat transfer medium oils; siloxane compounds such as polydimethylsiloxane, polymethylphenylsiloxane, polydiphenylsiloxane and silicone oils; and polyethers such as polypropylene glycol and polybutylene glycol. The number of carbon atoms should be 8 or more, although taking into consideration the dispersion stability of the particles to be obtained, the number of carbon atoms is preferably at least 10, more preferably at least 12, and most preferably at least 15.

In addition, the molecular weight of the hydrophobic organic solvent is preferably at least 200, more preferably at least 300, even more preferably at least 500, and most preferably at least 1,000. By thus using a hydrophobic organic solvent having a high molecular weight, the solvent also carries out a dispersant-like role, minimizing sticking and agglomeration of the particles and making it possible to obtain elliptical, needle-shaped or rod-shaped polymer particles that are stably monodispersed and have a controlled particle size.

In this invention, "molecular weight" refers to, in the case of high-molecular-weight compounds, the weight-average molecular weight. The weight-average molecular weight is a polystyrene-equivalent measured value obtained by gel permeation chromatography.

High-molecular-weight compounds having recurring units are preferred as the hydrophobic organic solvent with a molecular weight of 200 or more. Specific examples include siloxane compounds such as polydimethylsiloxane, polymethylphenylsiloxane, polydiphenylsiloxane and silicone oils; polyethers such as polypropylene glycol and polybutylene glycol; and aliphatic or aromatic hydrocarbons such as liquid paraffin and heat transfer medium oils. These high-molecular-weight compounds are more preferably high-molecular-weight compounds which are water-soluble in a low-molecular-weight state and exhibit hydrophobicity as the molecular weight increases, or hydrophobic organic solvents obtained by polymerizing a monomer having a polar group at the interior of the molecule. By having such polar groups at the interior of the molecule, the subsequently described high-molecular-weight stabilizer readily disperses uniformly within the solvent, further contributing to particle stability. Examples of such polar groups include hydroxyl, ether and carbonyl groups.

Examples of such preferred hydrophobic organic solvents include polyethers such as polypropylene glycol and polybutylene glycol; and siloxane compounds such as polydimethylsiloxane, polymethylphenylsiloxane, polydiphenylsiloxane and silicone oils.

The mixing ratio of the water, the hydrophilic organic solvent and the hydrophobic organic solvent, expressed as a weight ratio, is preferably from 99:0.5:0.5 to 25:55:20, more preferably from 98:1:1 to 35:50:15, and even more preferably from 97:2:1 to 45:45:10.

By using such a mixed solvent, there arises a "fuzzy" state within which co-exist an emulsified layer (bottom layer, or water-rich layer), a dissolved layer (intermediate layer, or hydrophilic solvent-rich layer) and a separated layer (top layer, or hydrophobic solvent-rich layer) that appear when the solvent is at rest; even in the polymerization reaction, the reaction is thought to proceed with the unsaturated monomer dissolved in each of these layers. It is surmised that, in cases where the polymerization reaction is carried out in a solvent system that forms this fuzzy state, when polymerization is induced by an initiator, the solvent dissolution balance due to heat breaks down and the tension at the particle separation boundary changes, enabling elliptical, needle-shaped or rod-shaped polymer particles to be obtained in a stably dispersed state; along with this, setting the pH of the synthesis solution to a specific value stably promotes the particle growth reactions, enabling the target polymer particles to be efficiently and more stably obtained.

The high-molecular-weight stabilizer is exemplified by various types of hydrophobic or hydrophilic stabilizers, including polyethylene glycol and polystyrene derivatives such as polyhydroxystyrene, polystyrene sulfonic acid, hydroxystyrene-(meth)acrylic ester copolymers, styrene-(meth)acrylic ester copolymers and styrene-hydroxystyrene-(meth)acrylic ester copolymers; poly(meth)acrylic acid and poly(meth)acrylic acid derivatives such as poly(meth)acrylamide, polyacrylonitrile, polyethyl (meth)acrylate and polybutyl (meth)acrylate; polyethers and derivatives thereof, such as poly(methyl vinyl ether), poly(ethyl vinyl ether), poly(butyl vinyl ether), poly(isobutyl vinyl ether) and poly(hexyl vinyl ether); cellulose and cellulose derivatives such as methyl cellulose, cellulose acetate, cellulose nitrate, hydroxymethyl cellulose, hydroxyethyl cellulose, hydroxypropyl cellulose and carboxymethyl cellulose; polyvinyl alcohol, polyvinyl butyral, polyvinyl formal and polyvinyl acetate derivatives such as polyvinyl acetate; nitrogen-containing polymer derivatives such as polyvinyl pyridine, polyvinyl pyrrolidone, polyethyleneimine and poly-2-methyl-2-oxazoline; and polyvinyl halide derivatives such as polyvinyl chloride and polyvinylidene chloride. These may be of one type used alone or two or more may be used in combination.

The high-molecular-weight stabilizer is preferably included in a suitable amount of from 0.01 to 50 wt %, based on the starting unsaturated monomer.

Various known polymerization initiators may be used as the polymerization initiator. Examples include the following water-soluble or ionic polymerization initiators: persulfates such as ammonium persulfate, sodium persulfate and potassium persulfate; and azo-type initiators such as 2,2'-azobis[2-methyl-N-(2-hydroxyethyl)propionamide], 2,2'-azobis(2-amidinopropane) dihydrochloride, 2,2'-azobis(2-methyl-N-phenylpropionamidine) dihydrochloride, 2,2'-azobis[N-(4-chlorophenyl)-2-methylpropionamidine] dihydrochloride, 2,2'-azobis[N-(4-hydroxyphenyl)-2-methylpropionamidine] dihydrochloride, 2,2'-azobis[N-(4-aminophenyl)-2-methylpropionamidine] tetrahydrochloride, 2,2'-azobis[2-methyl-N-(phenylmethyl)propionamidine] dihydrochloride, 2,2'-azobis[2-methyl-N-2-propenylpropionamidine] dihydrochloride, 2,2'-azobis[N-(2-hydroxyethyl)-2-methylpropionamidine] dihydrochloride, 2,2'-azobis[2-(5-methyl-2-imidazolin-2-yl)propane] dihydrochloride, 2,2'-azobis[2-(2-imidazolin-2-yl)propane] dihydrochloride, 2,2'-azobis[2-(4,5,6,7-tetrahydro-1H-1,3-diazepin-2-yl)propane] dihydrochloride, 2,2'-azobis[2-(3,4,5,6-tetrahydropyrimidin-2-yl)propane] dihydrochloride, 2,2'-azobis[2-(5-hydroxy-3,4,5,6-tetrahydropyrimidin-2-yl)propane] dihydrochloride, 2,2'-azobis {2-[1-(2-hydroxyethyl)-2-imidazolin-2-yl] propane} dihydrochloride, 2,2'-azobis-2-cyanopropane-1-sulfonic acid disodium salt, and sodium 4,4'-azobis(4-cyanopentanoate).

Examples of oil-soluble polymerization initiators include peroxides such as benzoyl peroxide, cumene hydroperoxide and t-butyl hydroperoxide; and azo compounds such as azobisisobutyronitrile, azobismethylbutyronitrile, azobisisovaleronitrile, 2,2'-azobis(dimethyl isobutyrate), 2,2'-azobis(N-butyl-2-methylpropionamide), 4,4'-azobis(4-cyanopentanoic acid), 2,2'-azobis(2-amidinopropane) dihydrochloride and 2,2'-azobis(N,N'-dimethylene isobutylamidine) dihydrochloride.

These polymerization initiators may be used singly or two or more may be used in admixture. It is preferable for the content of the radical polymerization initiator to be generally from 0.01 to 50 parts by weight per 100 parts by weight of the starting unsaturated monomer.

Of these, by using an initiator such as a persulfate, not only does this compound function as a radical initiator, an acid forms by hydrolysis or the like, making it possible to adjust the pH of the synthesis solution without having to separately add a pH adjustor. The preferred amount of addition is from 5 to 30 wt %.

It is possible to impart characteristics such as fine surface irregularities, porosity and a large specific surface area to the elliptical, needle-shaped or rod-shaped polymer particles by suitably adjusting the water, hydrophilic organic solvent and hydrophobic organic solvent ingredients and composition. The particle surface and interior can be suitably modified in this way.

In this invention, by carrying out the above types of adjustments in the solvent composition, it is possible to more stably control the particle size and aspect ratio, the size of fine surface irregularities, and the porosity of the elliptical, needle-shaped or rod-shaped polymer particles, enabling a good balance in performance attributes such as the water absorption and oil absorption to be achieved in accordance with the intended use.

When producing the elliptical, needle-shaped or rod-shaped polymer particles of the invention, an emulsifying agent (surfactant) may be optionally included in a suitable amount of from 0.01 to 50 wt %, based on the starting unsaturated monomer.

The emulsifying agent (surfactant) is exemplified by anionic emulsifying agents, including alkyl sulfates such as sodium dodecyl sulfate, alkylbenzenesulfonates such as sodium dodecylbenzenesulfonate, alkylnaphthalenesulfonates, fatty acid salts, alkyl phosphates and alkyl sulfosuccinates; cationic emulsifying agents such as alkylamine salts, quaternary ammonium salts, alkyl betaines and amine oxides; and nonionic emulsifying agents such as polyoxyethylene alkyl ethers, polyoxyethylene alkyl allyl ethers, polyoxyethylene alkyl phenyl ethers, sorbitan fatty acid esters, glycerol fatty acid esters, sucrose fatty acid esters and polyoxyethylene fatty acid esters. These may be used singly or two or more may be used in combination.

By adding an emulsifying agent, the length and breadth of the elliptical, needle-shaped or rod-shaped polymer particles can be controlled. In addition, it is preferable to include at least one emulsifying agent that is solid at room temperature.

The content of starting unsaturated monomer in the synthesis solution is preferably set to from 1 to 80 wt %, more preferably from 5 to 50 wt %, and even more preferably from 10 to 30 wt %, of the overall synthesis solution. At a starting unsaturated monomer content greater than 80 wt %, agglomerates increase and obtaining, in a monodispersed state, a high yield of polymer particles having the above properties may be difficult. On the other hand, at a content below 1 wt %, completion of the reaction takes a long time and is impractical from an industrial standpoint.

The reaction temperature during polymerization varies depending on the type of solvent used, and therefore cannot be strictly specified, but is typically from about 10° C. to about 200° C., preferably from 30 to 130° C., and more preferably from 40 to 90° C.

The reaction time is not particularly limited, so long as it is the time needed for the intended reaction to go substantially to completion, and is governed largely by such factors as the type and content of the unsaturated monomer, the viscosity and concentration of the solution, and the intended particle size. For example, at from 40 to 90° C., the reaction time is typically from 1 to 72 hours, and preferably from about 2 hours to about 24 hours.

Depending on such considerations as the intended use of the resulting particles, a catalyst (reaction accelerator) may be included at the time of the polymerization reaction. The content may be set to a suitable amount that does not adversely affect the particle properties, such as from 0.01 to 20 wt % of the total weight of the polymerization ingredients.

The catalyst is not particularly limited so long as it is a positive catalyst, and may be suitably selected from among known catalysts and used. Examples include tertiary amines such as benzyldimethylamine, triethylamine, tributylamine, pyridine and triphenylamine; quaternary ammonium compounds such as triethylbenzylammonium chloride and tetramethylammonium chloride; phosphines such as triphenylphosphine and tricyclophosphine; phosphonium compounds such as benzyl trimethylphosphonium chloride; imidazole compounds such as 2-methylimidazole and 2-methyl-4-ethylimidazole; alkali metal hydroxides such as potassium hydroxide, sodium hydroxide and lithium hydroxide; alkali metal carbonates such as sodium carbonate and lithium carbonate; alkali metal salts of organic acids; and halides that exhibit Lewis acid properties, such as boron trichloride, boron trifluoride, tin tetrachloride and titanium tetrachloride, or complex salts thereof. These may be used singly or two or more may be used in combination.

At the time of the polymerization reaction, in order to adjust the size, shape, quality and the like of the resulting elliptical, needle-shaped or rod-shaped polymer particles, it is also possible to add a compound that is soluble in water or another polar solvent and undergoes electrolytic dissociation into cations and anions, such that the solution exhibits electrical conductivity.

Such compounds are exemplified by salts, inorganic acids, inorganic bases, organic acids, organic bases and ionic liquids. The content is a suitable amount that does not adversely affect the particle properties, and may be set to, for example, from 0.01 to 80 wt % of the total weight of the polymerization ingredients.

By varying the types and weight ratios of the unsaturated monomer, high-molecular-weight stabilizer and solvent, and the weight ratios of the optionally used dispersant and emulsifying agent, elliptical, needle-shaped or rod-shaped polymer particles of differing particle sizes, aspect ratios, shapes and the like can be more stably produced in a monodispersed state.

[Crosslinking Step]

The production method of the invention may include, after the solution polymerization step, the step of crosslinking the resulting elliptical, needle-shaped or rod-shaped polymers with an organic compound having a reactive group that reacts with the reactive functional group by reacting functional groups included on the elliptical, needle-shaped or rod-shaped polymer particles with reactive groups included on the organic compound in the presence of a solvent that dissolves the organic compound but does not dissolve the elliptical, needle-shaped or rod-shaped polymer particles. At this time, the resulting elliptical, needle-shaped or rod-shaped polymer particles are particles obtained using the above-described Unsaturated Monomer B.

The solvent used in the crosslinking step may be the same as the above-described synthesis solvent. Illustrative examples include water, deionized water and distilled water; hydrophilic organic solvents such as methanol, ethanol, 1-propanol, 2-propanol, ethylene glycol, propylene glycol, butylene glycol, dipropylene glycol, methyl cellosolve, ethyl cellosolve, propyl cellosolve, methyl cellosolve acetate, ethyl cellosolve acetate, methyl carbitol, ethyl carbitol, butyl carbitol, ethyl carbitol acetate, acetone, tetrahydrofuran (THF), dimethyl formamide (DMF), N-methyl-2-pyrrolidone (NMP) and acetonitrile; and hydrophobic organic solvents, such as higher alcohols (e.g., 1-butanol, 2-butanol, isobutanol, t-butanol, 1-pentanol, 2-pentanol, 3-pentanol, 2-methyl-1-butanol, isopentyl alcohol, t-pentyl alcohol, 1-hexanol, 2-methyl-1-pentanol, 4-methyl-2-pentanol, 2-ethylbutanol, 1-heptanol, 2-heptanol, 3-heptanol, 2-octanol, 2-ethyl-1-hexanol, benzyl alcohol, cyclohexanol), ether alcohols (e.g., butyl cellosolve), polyethers (e.g., polypropylene glycol, polybutylene glycol), ketones (e.g., methyl ethyl ketone (MEK), methyl isobutyl ketone (MIBK), cyclohexanone), esters (e.g., ethyl acetate, butyl acetate, ethyl propionate, butyl carbitol acetate), aliphatic or aromatic hydrocarbons (e.g., pentane, 2-methylbutane, n-hexane, cyclohexane, 2-methylpentane, 2,2-dimethylbutane, 2,3-dimethylbutane, heptane, n-octane, isooctane, 2,2,3-trimethylpentane, decane, nonane, cyclopentane, methyl cyclopentane, methyl cyclohexane, ethyl cyclohexane, p-menthane, dicyclohexyl, benzene, toluene, xylene, ethylbenzene, liquid paraffin, oils), siloxane compounds (e.g., polydimethylsiloxane, polymethylphenylsiloxane, polydiphenylsiloxane), and halogenated hydrocarbons (e.g., carbon tetrachloride, trichloroethylene, chlorobenzene, tetrabromoethane). These may be used singly or two or more may be used in combination.

Of these, water (including deionized water, distilled water); lower alcohols such as methanol, ethanol and propanol; polyfunctional alcohols such as ethylene glycol, propylene glycol, butylene glycol and dipropylene glycol; ether alcohols such as methyl cellosolve and ethyl cellosolve; toluene, DMF, THF, MEK, MIBK, acetone, NMP, dichloromethane, tetrachloroethylene, and mixtures thereof are preferred. In particular, it is preferable to use a medium that includes at least a mixed solvent of water and a lower alcohol, a mixed solvent of water and a polyfunctional alcohol, or a mixed solvent of water and an ether alcohol.

The organic compound is preferably a compound containing two or more functional groups which react with the reactive functional groups included in the elliptical, needle-shaped or rod-shaped polymer particles.

The functional group included in the organic compound is preferably at least one selected from among hydroxyl, carboxyl, amino, thiol, carbonyl, ether, cyano, epoxy, amide, isocyanate, carbodiimide and oxazoline groups. These are also excellent for industrial use because they are widely used functional groups, promotion of the reaction at a relatively low temperature is possible, and the catalysts that are suitably used are relatively inexpensive. Of these, the most preferred functional groups include epoxy, amino, oxazoline, carbodiimide and isocyanate groups.

The organic compound is exemplified as follows. Examples of hydroxyl group-containing compounds include glycerol, 1,1,1-trimethylolpropane, 1,2,5-hexanetriol, 1,3- butanediol, 1,4-butanediol, 4,4'-dihydroxyphenylpropane, 4,4'-dihydroxyphenylmethane, pentaerythritol, phenolic resins and polyvinyl alcohol.

Examples of carboxyl group-containing compounds include oxalic acid, malonic acid, dimethyl malonate, diethyl malonate, succinic acid, glutaric acid, adipic acid, pimelic acid, suberic acid, azelaic acid, sebacic acid, phthalic acid, isophthalic acid, terephthalic acid, pentanetricarboxylic acid, hexanetricarboxylic acid, butanetetracarboxylic acid, hexanetetracarboxylic acid, cyclobutanedicarboxylic acid, cyclopentanedicarboxylic acid, cyclopentanetricarboxylic acid, cyclohexanetricarboxylic acid, cyclobutanetetracarboxylic acid, cyclohexanetetracarboxylic acid, cyclohexanehexacarboxylic acid, hydroxy acids, amino acids, malic acid, tartaric acid, citric acid, isocitric acid, aspartic acid, glutamic acid, carboxyl group-containing resins, and modified forms thereof.

Examples of amino group-containing compounds include polyimide resins obtained by polymerizing a diamine such as o-phenylenediamine, m-phenylenediamine, p-phenylenediamine, 4,4'-diaminodiphenyl ether, 1,4-bis(aminomethyl)cyclohexane, 1,3-bis(aminomethyl)cyclohexane, 1,3-propanediamine, 1,4-butanediamine, 1,5-pentanediamine or 1,6-hexanediamine with a tetracarboxylic dianhydride such as 4,4'-hexafluoropropylidenebisphthalic dianhydride, 4,4'-biphthalic anhydride, diphenyl-2,3,3',4'-tetracarboxylic dianhydride, diphenyl-2,2',3,3'-tetracarboxylic dianhydride or pyromellitic dianhydride.

Additional examples include aliphatic polyfunctional amines, aromatic polyfunctional amines, heterocyclic polyfunctional amines and aminoalkyl heterocyclic polyfunctional amines, such as ethylenediamine, diethylenetriamine, 1,4-cyclohexanediamine, isophoronediamine, tolylenediamine, cis-1,3-diaminocyclobutane, piperazine, hexamethylenediamine, m-xylylenediamine and aminoethylpiperazine. Also, examples of polyfunctional amino polymers include polyethyleneimine, polyallylamine, polydimethylallylammonium hydroxide, copolymers of these with acrylamide or sulfur dioxide, and polyfunctional amino copolymers of chitosan.

Examples of thiol group-containing compounds include methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, bicyclo[2,2,1]hepta-exo-cis-2,3-dithiol, ethylene glycol bisthioglycolate, butylene glycol bisthioglycolate, 4,4'-thiobisbenzenethiol, bis(4-mercaptophenyl) ether, 3,4-dimercaptotoluene, 2,5-toluenedithiol, 3,4-toluenedithiol, 1,4-naphthalenedithiol, 1,5-naphthalenedithiol, 2,6-naphthalenedithiol, 2,7-naphthalenedithiol, 2,4-dimethylbenzene-1,3-dithiol, 4,5-dimethylbenzene-1,3-dithiol, 1,3-di(p-methoxyphenyl)propane-2,2-dithiol, 1,3-diphenylpropane-2,2-dithiol, phenylmethane-1,1-dithiol, 2,4-di(p-mercaptophenyl)pentane, 6-dibutylamino-1,3,5-triazine-2,4-dithiol, 6-aminophenyl-1,3,5-triazine-2,4-dithiol, 2,5-dimercapto-1,2,4-thiadiazole, 2-methylamino-4,6-dithiol-sym-triazine, 2-ethylamino-4,6-dithiol-sym-triazine, 2-amino-4,6-dithiol-sym-triazine, 2-morpholino-4,6-dithiol-sym-triazine, 2-cyclohexylamino-4,6-dithiol-sym-triazine, 2-methoxy-4,6-dithiol-sym-triazine, 2-phenoxy-4,6-dithiol-sym-triazine, 2-thiobenzeneoxy-4,6-dithiol-sym-triazine, 2-thiobutyloxy-4,6-dithiol-sym-triazine, thiol group-containing resins, and modified forms thereof.

Examples of carbonyl group-containing compounds include diacetyl, acetylacetone, methyl acetoacetate, ethyl acetoacetate, dimedone, 2,4-hexanedione, 2,4-heptanedione, 3,5-heptanedione, 2,4-octanedione, 2,4-nonanedione, 5-methylhexanedione, 2,5-hexanedione, 2,2,6,6-tetramethyl-3,5-heptanedione, carbonyl group-containing resins, and modified forms thereof.

Examples of ether group-containing compounds include ethylene glycol dimethyl ether, diethylene glycol dimethyl ether, triethylene glycol dimethyl ether, tetraethylene glycol dimethyl ether, polyethylene glycol dimethyl ether, ethylene glycol diethyl ether, diethylene glycol diethyl ether, diethylene glycol dibutyl ether, diethylene glycol ethyl butyl ether, triethylene glycol dibutyl ether, tetraethylene glycol dibutyl ether, diethylene glycol dioctyl ether, diethylene glycol di-2-ethyl hexyl ether, dipropylene glycol diethyl ether, dipropylene glycol dimethyl ether, diethylene glycol 2-ethyl hexyl ether, diethylene glycol butyl-2-ethyl hexyl ether, tripropylene glycol dimethyl ether, tripropylene glycol diethyl ether, tripropylene glycol dibutyl ether, tripropylene isopropyl butyl ether, tripropylene glycol isopropyl ethyl ether, tetrapropylene glycol dipropyl ether, ether group-containing resins, and modified forms thereof.

Examples of cyano group-containing compounds include malononitrile, succinonitrile, glutaronitrile, adiponitrile, pimelonitrile, suberonitrile, azelanitrile, sebaconitrile, undecanedinitrile, dodecanedinitrile, methylmalononitrile, ethylmalononitrile, isopropylmalononitrile, t-butylmalononitrile, methylsuccinonitrile, 2,2-dimethylsuccinonitrile, 2,3-dimethylsuccinonitrile, 2,3,3-trimethylsuccinonitrile, 2,2,3,3-tetramethylsuccinonitrile, 2,3-diethyl-2,3-dimethylsuccinonitrile, 2,2-diethyl-3,3-dimethylsuccinonitrile, bicyclohexyl-1,1-dicarbonitrile, bicyclohexyl-2,2-dicarbonitrile, bicyclohexyl-3,3-dicarbonitrile, 2,5-dimethyl-2,5-hexanedicarbonitrile, 2,3-diisobutyl-2,3-dimethylsuccinonitrile, 2,2-diisobutyl-3,3-dimethylsuccinonitrile, 2-methylglutaronitrile, 2,3-dimethylglutaronitrile, 2,4-dimethylglutaronitrile, 2,2,3,3-tetramethylglutaronitrile, 2,2,4,4-tetramethylglutaronitrile, 2,2,3,4-tetramethylglutaronitrile, 2,3,3,4-tetramethylglutaronitrile, maleonitrile, fumaronitrile, 1,4-dicyanopentane, 2,6-dicyanoheptane, 2,7-dicyanooctane, 2,8-dicyanononane, 1,6-dicyanodecane, 1,2-dicyanobenzene, 1,3-dicyanobenzene, 1,4-dicyanobenzene, 3,3'-(ethylenedioxy)dipropionitrile, 3,3'-(ethylenedithio)dipropionitrile, cyano group-containing resins, and modified forms thereof.

Exemplary epoxy group-containing compounds include polyepoxides, aromatic polyepoxy compounds, glycidyl ethers of polyhydric phenols, glycidyl esters of polyhydric phenols, glycidyl aromatic polyamines, alicyclic polyepoxy compounds, aliphatic polyepoxy compounds, and polyglycidyl esters of polyunsaturated fatty acids. Of these, aliphatic polyepoxy compounds and aromatic polyepoxy compounds are preferred.

Specific examples of epoxy group-containing compounds include glycidyl ethers of aliphatic polyhydric alcohols, such as neopentyl glycol diglycidyl ether, 1,6-hexanediol diglycidyl ether, ethylene glycol diglycidyl ether, propylene glycol diglycidyl ether, hexamethylene glycol diglycidyl ether, cyclohexanediol diglycidyl ether, glycerol triglycidyl ether, trimethylolpropane triglycidyl ether and pentaerythritol tetraglycidyl ether; glycidyl ethers of polyalkylene glycols, such as polyethylene glycol diglycidyl ether, polypropylene glycol diglycidyl ether and polytetramethylene glycol diglycidyl ether; polyglycidylated polyester resins; polyglycidylated polyamide resins; bisphenol A epoxy resins; phenol-novolak epoxy resins; and epoxy urethane resins.

Commercial products may also be used as the epoxy group-containing compound. Examples include the following from Nagase ChemteX Corporation: Denacol EX-611, 612, 614, 614B, 622, 512, 521, 411, 421, 313, 314, 321, 201, 211, 212, 252, 810, 811, 850, 851, 821, 830, 832, 841, 861, 911, 941, 920, 931, 721, 111, 212L, 214L, 216L, 321L, 850L, 1310, 1410, 1610 and 610U, and also epoxy compounds corresponding thereto. These may be used singly or two or more may be used in combination.

Examples of amide group-containing compounds include polyamide resins obtained by the polycondensation of a dicarboxylic acid such as adipic acid, heptanedicarboxylic acid, octanedicarboxylic acid, nonanedicarboxylic acid, undecanedicarboxylic acid or dodecanedicarboxylic acid with a diamine such as tetramethylenediamine, hexamethylenediamine, octamethylenediamine, nonamethylenediamine, undecamethylenediamine or dodecamethylenediamine. Further examples include polyamide resins obtained by the ring-opening polymerization of α-pyrrolidone, ε-caprolactam, ω-laurolactam, or ε-enantholactam. Specific examples include nylon-6, nylon-11, nylon-12, nylon-6,6 and nylon-6,T. Exemplary amino resins include urea resins, melamine resins and guanamine resins.

Examples of isocyanate group-containing compounds include polyisocyanates such as 4-tolylene diisocyanate, 2,6-tolylene diisocyanate, 4,4'-diphenylmethane diisocyanate, 2,4'-diphenylmethane diisocyanate, p-phenylene diisocyanate, isophorone diisocyanate and xylylene diisocyanate.

Examples of carbodiimide group-containing compounds include resins having at least one carbodiimide group that can be obtained using one, two or more isocyanate compounds as the starting materials.

Exemplary oxazoline group-containing compounds include bisoxazoline compounds and compounds having a terminal oxazoline group that can be obtained by reacting two chemical equivalents of oxazoline groups on a bisoxazoline compound with one chemical equivalent of carboxyl groups on a polybasic carboxylic acid. The oxazoline compound may also be a polymerized compound having at least two oxazoline groups per molecule obtained from a polymer by, for example, addition polymerization without ring opening of the oxazoline rings. Other exemplary oxazoline group-containing compounds include copolymers of an addition polymerizable oxazoline compound and a copolymerizable monomer that does not react with oxazoline groups.

Examples of compounds having two or more oxazoline rings include bisoxazoline compounds such as 2,2'-bis(2-oxazoline), 2,2'-bis(4-methyl-2-oxazoline), 2,2'-bis(5-methyl-2-oxazoline), 2,2'-bis(5,5'-dimethyloxazoline), 2,2'-bis(4,4,4',4'-tetramethyl-2-oxazoline), 1,2-bis(2-oxazolin-2-yl)ethane, 1,4-bis(2-oxazolin-2-yl)butane, 1,6-bis(2-oxazolin-2-yl)hexane, 1,4-bis(2-oxazolin-2-yl)cyclohexane, 1,2-bis(2-oxazolin-2-yl)benzene, 1,3-bis(2-oxazolin-2-yl)benzene, 1,4-bis(2-oxazolin-2-yl)benzene, 1,2-bis(5-methyl-2-oxazolin-2-yl)benzene, 1,3-bis(5-methyl-2-oxazolin-2-yl)benzene, 1,4-bis(5-methyl-2-oxazolin-2-yl)benzene and 1,4-bis(4,4'-dimethyl-2-oxazolin-2-yl)benzene; and compounds having a terminal oxazoline group obtained by reacting two chemical equivalents of oxazoline groups on any of these bisoxazoline compounds with one chemical equivalent of carboxyl groups on a polybasic carboxylic acid (e.g., maleic acid, succinic acid, itaconic acid, phthalic acid, tetrahydrophthalic acid, hexahydrophthalic acid, methylhexahydrophthalic acid, chlorendic acid, trimellitic acid pyromellitic acid, benzophenonetetracarboxylic acid).

The oxazoline compound may also be a polymerized compound having at least two oxazoline groups per molecule obtained from a polymer by, for example, addition polymerization without ring opening of the oxazoline rings. Commercial products may be used as such compounds. Examples include Epocros® WS-500, WS-700, K-1010E, K-2010E, K-1020E, K-2020E, K-1030E, K-2030E and RPS-1005 from Nippon Shokubai Co., Ltd.

Of these, compounds having an epoxy, amino, oxazoline, carbodiimide or isocyanate group are preferred, and compounds having an epoxy, oxazoline or carbodiimide group are more preferred.

The organic compound has a molecular weight of preferably from 50 to 100,000, more preferably from 100 to 10,000, and even more preferably from 200 to 5,000. At a molecular weight greater than 100,000, it is difficult to induce curing reactions to the particle interior. Also, because the viscosity of the synthesis solution rises excessively, this may have an adverse effect on the monodispersed particles. On the other hand, at a molecular weight below 50, it may not be possible to display the performance of functional particles such as have a core/shell structure.

After the solution polymerization step and before the crosslinking step, the resulting elliptical, needle-shaped or rod-shaped polymer particles may be purified in the usual manner, following which the solvent and organic compound may be added and crosslinking carried out. Alternatively, crosslinking may be carried out by directly adding the organic compound after the solution polymerization step, without first carrying out purification.

[Elliptical, Needle-Shaped or Rod-Shaped Polymer Particles]

The $L_{AV}$ value for the polymer particles obtained by the method of the invention is from 0.1 to 80 μm, preferably from 0.2 to 60 μm, more preferably from 1.0 to 40 μm, and even more preferably from 2 to 30 m. When $L_{AV}$ is greater than 80 μm, the properties become no different from those of widely used fibers and so the particle loses its superiority. Also, the decrease in specific surface area per unit tends to be accompanied by a marked decrease in optical characteristics such as the light scattering properties. On the other hand, when $L_{AV}$ is less than 0.1 μm, the breadth of the particles also becomes small, which may lead to a decline in the optical characteristics and a decrease in strength.

The $D_{AV}$ value for the polymer particles is from 0.05 to 40 μm, preferably from 0.1 to 30 μm, more preferably from 0.5 to 20 μm, and even more preferably from 1 to 15 m. When $D_{AV}$ is greater than 40 μm, the properties become no different from those of widely used spherical particles. Also, the decrease in specific surface area per unit tends to be accompanied by a marked decrease in the optical characteristic effects. On the other hand, when $D_{AV}$ is less than 0.05 μm, the optical characteristics may decline and the strength may decrease.

The $P_{AV}$ value for the polymer particles is from 1.5 to 30, preferably from 1.8 to 25, more preferably from 2 to 20, and even more preferably from 2.2 to 20. In cases where optical characteristics such as the light scattering properties are of particular importance, it is best for $P_{AV}$ to be from 3 to 18. When $P_{AV}$ is greater than 30 μm, the resulting particles tend to orient themselves, as a result of which optical characteristics such as light scattering properties and light reflectivity cannot be stably obtained. On the other hand, when $P_{AV}$ is less than 1.5, only optical characteristic effects of the same degree as those by spherical particles made of the same ingredients are obtained, and so these polymer particles provide little advantage.

Also, the polymer particles have a volume mean particle size (MV) which is preferably from 0.06 to 50 µm, more preferably from 0.1 to 30 µm, and even more preferably from 0.5 to 20 µm. When MV is greater than 50 µm, the decrease in specific surface area per unit may be accompanied by a decrease in the optical characteristic effects. On the other hand, when MV is less than 0.06 µm, light may pass through, reducing the optical characteristic effects.

In this invention, "volume mean particle size" is a measured value obtained by the laser scattering diffraction method and refers to, in the case of elliptical, needle-shaped or rod-shaped particles or unusually shaped particles, the mean diameter of spheres having the same volumes as the particles (i.e., mean sphere-equivalent diameter of the particles).

The polymer particles obtained by the method of the invention preferably have characteristics that make the specific surface area relatively large, such as having fine irregularities at the particle surface or being porous. It is especially preferable for the particles to be porous.

The polymer particles obtained by the method of the invention preferably have a specific surface area that satisfies the following formula.

$$SB/SD \geq 1.2$$

Here, SB is the actual specific surface area of each particle, and SD is the theoretical specific surface area of a spherical particle calculated from the volume mean particle size of each particle.

The ratio SB/SD is preferably at least 1.5, more preferably at least 1.8, and most preferably at least 2.0. Owing to this large specific surface area, the crosslinking reactions proceed efficiently at the time of reaction.

The actual specific surface area SB of the polymer particles obtained by the method of the invention, although not particularly limited, is preferably from 0.1 to 30 $m^2/g$, more preferably from 0.5 to 20 $m^2/g$, and even more preferably from 1 to 10 $m^2/g$. The specific surface area SB is a value measured by the nitrogen gas adsorption method.

The polymer particles obtained by the method of the invention are preferably particles which have a water adsorption or oil adsorption of at least 50 mL per 100 g of particles, and have an affinity for aqueous systems, oil systems or both. The water adsorption or oil adsorption is more preferably at least 80 mL per 100 g of particles, even more preferably at least 100 g per 100 g of particles, and most preferably at least 120 mL per 100 g of particles.

The molecular weight of the polymer making up the particles is not particularly limited, although the weight-average molecular weight is typically from about 1,000 to about 3,000,000.

Also, when a resin composition containing the elliptical, needle-shaped or rod-shaped polymer particles of the invention is molded or formed into a light-diffusing plate or light-diffusing sheet, in order for these to manifest sufficient heat resistance even at elevated temperatures, it is preferable for the elliptical, needle-shaped or rod-shaped polymer particles to have a melting point of at least 60° C.

[Uses of Elliptical, Needle-Shaped or Rod-Shaped Polymer Particles]

The elliptical, needle-shaped or rod-shaped polymer particles obtained by the method of the invention have excellent heat and chemical resistances, and thus can be used in polymer molded or formed articles such as plastics, containers, paints, paint films, fibers and building materials. Also, because they are effective as well in terms of UV scattering properties, they can be used for the protection of UV-sensitive contents, such as in filters, packaging materials, containers, paints, paint films, inks, fibers, building materials, recording media, image displaying devices and solar cell covers, and can also check the decomposition of compounds unstable to light.

The elliptical, needle-shaped or rod-shaped polymer particles may be dispersed in water, a hydrophilic organic solvent, a hydrophobic organic solvent or a mixed solvent thereof and used as a dispersion. The hydrophilic organic solvent and hydrophobic organic solvent are exemplified by the same solvents mentioned above in connection with the polymer particle production method.

The elliptical, needle-shaped or rod-shaped polymer particles may be used as an additive in liquids and formed articles such as paint films, film, sheet stock and paper. The crosslinked polymer particle-containing compositions of the invention may be widely used in, for example, light scattering agents and optical filter materials, colorants, cosmetics, absorbents, adsorbents, inks, adhesives, electromagnetic shielding materials, fluorescence sensors, biological markers, recording media, recording elements, polarizing materials, drug supports for drug delivery systems (DDS), biosensors, DNA chips, diagnostic agents and thermally cavitated products having pores.

Also, by incorporating the crosslinked polymer particles of the invention into a precursor, and carrying out firing treatment such as curing, carbonization or sintering, a thermally cavitated product having particle-shaped pores can be produced.

Using window glass products or interior decoration products such as curtains and wall materials to block light or ultraviolet radiation from entering into a room, car or the like is useful not only for preventing sunburn and other adverse effects to the human body, but also for preventing the deterioration of decorative objects within the room or car.

The elliptical, needle-shaped or rod-shaped polymer particles of the invention are suitable as additives for cosmetics. Expansion into thermoforming applications and applications that use a large amount of organic solvent where addition has hitherto been difficult is now possible while retaining such desirable features of the elliptical, needle-shaped or rod-shaped polymer particles as their low weight and their light scattering properties, tactile qualities, flowability and solution dispersibility. The elliptical, needle-shaped or rod-shaped polymer particles of the invention, owing to their distinctive shapes, have an adhesive strength differing from that of ordinary spherical particles, and are thus effective for improving both the bonding strength of pressed compacts of cosmetic foundation and also the holding power following application. In addition, the optical characteristics make the skin appear lighter and can enhance the covering power due to a shading effect. Also, due to the slip properties particular to the particle shape, spreadability over the skin is excellent and furrows in the skin texture are finely filled, making wrinkles and pores inconspicuous, and the flowability of the overall product can be freely controlled. Also, the adhesive strength and holding power can be utilized to increase the amount of polymer addition in the overall product, enabling the discovery of entirely new cosmetic effects. The amount of addition, based on the product contents, is preferably from 0.1 to 50 wt %, and more preferably from 0.5 to 30 wt %. This amount may be suitably adjusted according to the intended use and purpose, such as enhancing the light scattering properties (e.g., the UV scattering effect and the shading effect), flowability, moldability and adhesion, and the finished look. According to studies by the inventors, as an additive for cosmetics, the addition of 1 to 20 wt % is especially preferred. Suitable adjustment and use in combination with commercially available particles is also possible.

Cosmetics in which the advantageous effects are high are exemplified in particular by skin care products, hair products, antiperspirants, makeup products, UV protection products and scented products. Specific examples include base cosmetics such as milky emulsions, creams, lotions, calamine lotion, sunscreens, makeup base, suntan lotions, aftershave lotions, preshave lotions, packs, cleansing materials, facial cleansers, cosmetics for acne, and essences; makeup cosmetics such as foundation, face powder, mascara, eye shadow, eyeliner, eyebrow, cheek, nail color, lip cream and lipstick; and also shampoos, rinses, conditioners, hair colors, hair tonics, setting agents, body powders, hair growth promoters, deodorants, depilatories, soaps, body shampoos, bath preparations, hand soaps and perfumes. The form of the product is not particularly limited and includes, for example, liquids, emulsions, creams, solids, pastes, gels, powders, multi-layer preparations, mousses and sprays. Useful effects can be expected of the crosslinked polymer particles as an additive in these cosmetics.

The elliptical, needle-shaped or rod-shaped polymer particles can be utilized as additives for printing inks that may be used in, for example, screen printing, offset printing, process printing, gravure printing, pad printing, coaters and inkjet printing; as additives for writing implement inks in marking pens, ballpoint pens, fountain pens, calligraphy pens and magic markers; and as additives for writing materials such as crayons, artist's paints and erasers.

The elliptical, needle-shaped or rod-shaped polymer particles are suitable as additives for paints that may be used in brush painting, spray painting, electrostatic spray painting, electrodeposition painting, flow coating, roller coating and dip coating. For example, they are suitable as additives for paints and coatings that may be used on transportation equipment such as automobiles, railway cars, helicopters, ships, bicycles, snowmobiles, ropeways, lifts, hovercrafts and motorcycles; building members such as window sashes, shutters, cisterns, doors, balconies, outside panels for construction, roofing, staircases, skylights and concrete walls; the exterior walls and interior finish on the inside and outside of buildings; roadway members such as guardrails, pedestrian bridges, sound insulating walls, road signs, highway sidewalls, elevated railway bridges, and bridges; industrial plant members such as tanks, pipes, towers and smokestacks; agricultural facilities such as PVC and other types of greenhouses, silos and agricultural sheeting; telecommunications facilities such as utility poles, transmission towers and parabolic antennas; electrical equipment such as electrical service boxes, lighting equipment, outdoor air conditioners, washing machines, refrigerators and electric ranges, as well as covers for these; and other articles such as monuments, gravestones, paving materials, windscreens, waterproof sheeting and curing sheets for construction.

The form of the paint is exemplified by not only solvent-based paints, but also water-dispersed paints, non-water-dispersed paints, powder paints and electrodeposition paints, and may be suitably selected as needed.

EXAMPLES

Synthesis Examples, Working Examples and Comparative Examples are given below by way of illustration, although the invention is not limited to these Examples. Evaluations in the Working Examples and Comparative Examples were carried out by the following methods.

(1) Aspect Ratio of Polymer Particles

A scanning electron microscope (S-4800, from Hitachi High Technologies Corporation; referred to below as "SEM") was used to capture photographs at a magnification at which particle measurement is possible (300 to 30,000×), thereby rendering the elliptical, needle-shaped or rod-shaped polymer particles obtained into two-dimensional images (elliptical, needle-shaped or rod-shaped polymer particles typically maintain a state in which the long axis direction is horizontally oriented). In the images, 100 particles were randomly sampled and the length (L) and breadth (D) of each particle were measured, the aspect ratio (L/D) for the particle was calculated, and the average aspect ratio ($P_{AV}$) was determined.

The average length ($L_{AV}$) and average breadth ($D_{AV}$) of the particles were similarly calculated after measuring the length (L) and breadth (D) of 100 randomly sampled particles.

(2) Volume Mean Particle Size (MV) of Polymer Particles

The volume mean particle size was measured using the MICROTRACK MT3000 (Nikkiso Co., Ltd.).

(3) Definition of Measured Agglomerates, and Measurement of Amounts Thereof

The measured agglomerates obtained at the time of synthesis are defined as follows.

Agglomerate 1: The matter obtained by passing the synthesis solution through a 200 m sieve, washing the agglomerate that remained on the sieve with a water-ethanol mixed solution, and drying the resulting component was called "Agglomerate 1."

Agglomerate 2: The matter obtained by scraping off polymer component (agglomerate) adhering to the interior of the synthesis vessel (the flask and the stirring element) into the vessel being used, carrying out dispersion/washing with a water-ethanol mixed solution, passing the mixture through a 200 m sieve, and drying what remains on the sieve was called "Agglomerate 2."

The agglomerate ratio (%) was determined by the following formula.

$$\text{Agglomerate ratio (\%)} = [(\text{Agglomerate 1} + \text{Agglomerate 2})/\text{total amount of component (monomer) rendered into particles}] \times 100$$

(4) pH Measurement

The pH was determined by visually judging the change in color using pH test paper (from Whatman).

Synthesis of Elliptical, Needle-Shaped or Rod-Shaped Polymer Particles

Working Example 1

A synthesis solution was prepared by charging the compounds shown below all at once into a 2,000 mL flask. The solution was then stirred at room temperature for one hour. The liquid phase was in a state where an aqueous phase portion, an emulsified phase portion and an oil phase portion are intermingled. The pH of the synthesis solution was measured and found to be 7. Next, under a stream of nitrogen, the solution was set to an oil bath temperature of 80° C. and heating and stirring (400 rpm) were begun. After 8 hours of heating and stirring (400 rpm), a polymethyl methacrylate particle dispersion was obtained. When the internal temperature reached 40° C. during this step, 1 mol/L hydrochloric acid was added dropwise for 15 minutes as a pH adjustor until the pH became 2. The pH at the time of reaction completion was also 2.

| | |
|---|---|
| Water | 1,280.0 g |
| Methanol | 38.4 g |
| Polypropylene glycol (#3000) | 9.0 g |
| Polyvinyl pyrrolidone (K-15) | 32.0 g |
| Sucrose ester of lauric acid | 10.5 g |
| Azobisisobutyronitrile (AIBN) | 8.6 g |
| Methyl methacrylate | 288.0 g |

The resulting particle dispersion was passed through a 200 m sieve and transferred to a separate 3,000 mL flask; the agglomerate that remained on the sieve was collected as Agglomerate 1 following treatment as described above. The polymer component (agglomerate) adhering to the interior of the synthesis vessel (the flask and stirring element) was scraped off into the vessel being used and collected as Agglomerate 2 following treatment as described above (the flask and stirring element used were clean, with substantially no deposits observable thereon).

Next, using a known suction filtration apparatus, the particle dispersion that passed through the sieve was repeatedly (5 times) washed with methanol and filtered, and then vacuum dried, giving Polymer Particle A1.

One hundred of the resulting particles were randomly sampled and their shapes examined with the SEM. The particles were found to be elliptical, needle-shaped or rod-shaped polymer particles. The $L_{AV}$ was 19.1 μm, and the $P_{AV}$ was 6.8.

The particles were checked for extraneous matter, but substantially no deformed matter such as agglomerates or mutually sticking particles was observed.

FIG. 1 shows a SEM micrograph of the resulting particles.

Working Example 2

Aside from changing the pH adjustor to 1 mol/L sodium hydroxide and adjusting the pH at the time of synthesis to 12, a polymethyl methacrylate particle dispersion was obtained in the same way as in Working Example 1. The pH at the time of reaction completion was also 12.

The resulting particle dispersion was passed through a 200 m sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with methanol and filtered, and then vacuum dried, giving Polymer Particle A2.

One hundred of the resulting particles were randomly sampled and their shapes examined with the SEM. The particles were found to be elliptical, needle-shaped or rod-shaped polymer particles. The $L_{AV}$ was 23.5 μm, and the $P_{AV}$ was 7.4.

The particles were checked for extraneous matter, but substantially no deformed matter such as agglomerates or mutually sticking particles was observed.

Working Example 3

Aside from changing the azobisisobutyronitrile to 16.0 g of ammonium persulfate and not using a pH adjustor, a polymethyl methacrylate particle dispersion was obtained in the same way as in Working Example 1. The pH before the start of heating was 7, the pH two hours after the start of heating was 2, and the pH at the time of reaction completion was 1.

The resulting particle dispersion was passed through a 200 μm sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with methanol and filtered, and then vacuum dried, giving Polymer Particle A3.

One hundred of the resulting particles were randomly sampled and their shapes examined with the SEM. The particles were found to be elliptical, needle-shaped or rod-shaped polymer particles. The $L_{AV}$ was 17.8 μm, and the $P_{AV}$ was 5.9.

The particles were checked for extraneous matter, but substantially no deformed matter such as agglomerates or mutually sticking particles was observed.

Working Example 4

The compounds shown below were charged all at once into a 2,000 mL flask and stirred at room temperature for one hour. The liquid phase was in a state where an aqueous phase portion, an emulsified phase portion and an oil phase portion are intermingled. The pH of the synthesis solution was measured and found to be 7. Next, under a stream of nitrogen, the solution was set to an oil bath temperature of 80° C. and heating and stirring (400 rpm) were begun. After 8 hours of heating and stirring (400 rpm), a styrene-sodium p-styrenesulfonate copolymer particle dispersion was obtained. When the internal temperature reached 40° C. during this step, 1 mol/L hydrochloric acid was added dropwise to the synthesis solution for 15 minutes as a pH adjustor until the pH became 12. The pH at the time of reaction completion was also 12.

| | |
|---|---|
| Water | 768.0 g |
| Methanol | 512.0 g |
| Polypropylene glycol (#3000) | 32.0 g |
| Polyvinyl pyrrolidone (K-15) | 48.0 g |
| Sorbitan monooleate | 8.0 g |
| Azobisisobutyronitrile (AIBN) | 30.0 g |
| Styrene | 240.0 g |
| Sodium p-styrenesulfonate | 60.0 g |

The resulting particle dispersion was passed through a 200 m sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with methanol and filtered, and then vacuum dried, giving Polymer Particle A4. The makeup (molar ratio) of the recurring units in Polymer Particle A4 was styrene:sodium p-styrenesulfonate=89:11.

One hundred of the resulting particles were randomly sampled and their shapes examined with the SEM. The particles were found to be elliptical, needle-shaped or rod-shaped polymer particles. The $L_{AV}$ was 29.4 μm, and the $P_{AV}$ was 8.4.

The particles were checked for extraneous matter, but substantially no deformed matter such as agglomerates or mutually sticking particles was observed.

Working Example 5

A synthesis solution was prepared by charging the compounds shown below all at once into a 2,000 mL flask. The solution was then stirred at room temperature for one hour. The liquid phase was in a state where an aqueous phase portion, an emulsified phase portion and an oil phase portion are intermingled. The pH of the synthesis solution was measured and found to be 6. Next, under a stream of nitrogen, the solution was set to an oil bath temperature of 80° C. and heating and stirring (400 rpm) were begun. After 8 hours of heating and stirring (400 rpm), a styrene-2-hydroxyethyl methacrylate copolymer particle dispersion was obtained. When the internal temperature reached 40° C. during this step, 1 mol/L hydrochloric acid was added dropwise to the synthesis solution for 15 minutes as a pH adjustor until the pH became 2. The pH at the time of reaction completion was also 2.

| | |
|---|---:|
| Water | 768.0 g |
| Methanol | 512.0 g |
| Polypropylene glycol (#3000) | 15.0 g |
| Polyvinyl pyrrolidone (K-30) | 24.0 g |
| Polyethylene glycol (PEG 20000) | 6.4 g |
| Azobisisobutyronitrile (AIBN) | 12.0 g |
| Styrene | 80.0 g |
| 2-Hydroxyethyl methacrylate | 120.0 g |

The resulting particle dispersion was passed through a 200 μm sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with a mixed solution of methanol and water (weight ratio=7:3) and filtered, and then vacuum dried, giving Polymer Particle A5. The makeup (molar ratio) of the recurring units in Polymer Particle A5 was styrene:2-hydroxyethyl methacrylate=46:54.

One hundred of the resulting particles were randomly sampled and their shapes examined with the SEM. The particles were found to be elliptical, needle-shaped or rod-shaped polymer particles. The $L_{AV}$ was 51.2 μm, and the $P_{AV}$ was 10.2.

The particles were checked for extraneous matter, but substantially no deformed matter such as agglomerates or mutually sticking particles was observed.

Comparative Example 1

A synthesis solution was prepared by dissolving the compounds shown below in the respective phases, mixing together the aqueous phase and the oil phase, and charging the mixture into a 2,000 mL flask. The synthesis solution was then stirred for one hour and subsequently, under a stream of nitrogen, was set to an oil bath temperature of 80° C. and heated and stirred for 12 hours, giving a polymethyl methacrylate particle dispersion. The pH of the synthesis solution before the start of heating was 7, the pH two hours after the start of heating was 6, and the pH at the time of reaction completion was 6.

| | |
|---|---:|
| Aqueous Phase | |
| Water | 1,280.0 g |
| Polyvinyl pyrrolidone (K-15) | 8.0 g |
| Ammonium persulfate | 4.8 g |
| Oil Phase | |
| Toluene | 80.0 g |
| Polystyrene (Mw, 45,000) | 16.0 g |
| Methyl methacrylate | 160.0 g |

(Polystyrene: Polystyrene from Aldrich Co.; average Mw, ca. 45,000)

The resulting particle dispersion was passed through a 200 m sieve and transferred to a separate 3,000 mL flask. Agglomerates 1 and 2 were collected in the same way as in Working Example 1 (masses of agglomerate were observed on the inner periphery of the flask and stirring element used).

Next, using a known suction filtration apparatus, the particle dispersion that passed through the sieve was repeatedly (5 times) washed with methanol and filtered, and then vacuum dried, giving Polymer Particle B1.

The shapes of the resulting particles were examined with the SEM, whereupon elliptical, needle-shaped or rod-shaped polymer particles were observed here and there, but large numbers of agglomerates and extraneous matter that passed through the 200 m sieve were also observed in places. Hence, the process used here cannot be regarded as a method that stably and efficiently produces elliptical, needle-shaped or rod-shaped polymer particles. FIG. 2 shows an SEM micrograph of the particles obtained.

One hundred of the resulting particles were randomly sampled and measured. The $L_{AV}$ was 31.2 μm, and the $P_{AV}$ was 6.9.

Comparative Example 2

A synthesis solution was prepared by charging the compounds shown below all at once into a 2,000 mL flask. Dissolved oxygen was removed by purging with nitrogen, following which the solution was stirred and heated for about 12 hours at an oil bath temperature of 88° C. under a stream of nitrogen, giving a styrene-sodium p-styrenesulfonate copolymer particle dispersion. The pH of the synthesis solution before the start of heating was 7, the pH two hours after the start of heating was 8, and the pH at the time of reaction completion was also 8.

| | |
|---|---:|
| Styrene | 240.0 g |
| Sodium p-styrenesulfonate | 60.0 g |
| Butanol | 400.0 g |
| Methanol | 200.0 g |
| Water | 600.0 g |
| Azobisisobutyronitrile (AIBN) | 30.0 g |
| Polyvinyl pyrrolidone (K-30) | 250.0 g |
| Sodium dodecyl sulfate | 6.0 g |

The resulting particle dispersion was passed through a 200 μm sieve and transferred to a separate 3,000 mL flask. Agglomerates 1 and 2 were collected in the same way as in Working Example 1 (masses of agglomerate were observed on the inner periphery of the flask and stirring element used).

Next, using a known suction filtration apparatus, the particle dispersion that passed through the sieve was repeatedly (5 times) washed with methanol and filtered, and then vacuum dried, giving Polymer Particle B2. The makeup (molar ratio) of the recurring units in Polymer Particle B2 was styrene:sodium p-styrenesulfonate=89:11.

The shapes of the resulting particles were examined with the SEM, whereupon elliptical, needle-shaped or rod-shaped polymer particles were observed here and there, but large numbers of agglomerates and extraneous matter that passed through the 200 μm sieve were also observed in places. Hence, the process used here cannot be regarded as a method that stably and efficiently produces elliptical, needle-shaped or rod-shaped polymer particles.

One hundred of the resulting particles were randomly sampled and measured. The $L_{AV}$ was 22.7 μm, and the $P_{AV}$ was 6.2.

Comparative Example 3

Aside from not carrying out pH adjustment, a polymethyl methacrylate particle dispersion was obtained in the same way as in Working Example 1. The pH of the synthesis solution before the start of heating was 7, the pH two hours after the start of heating was 7, and the pH at the time of reaction completion was also 7.

The resulting particle dispersion was passed through a 200 m sieve and transferred to a separate 3,000 mL flask. Agglomerates 1 and 2 were collected in the same way as in Working Example 1 (masses of agglomerate where some polymer had deposited were observed on the inner periphery of the flask and stirring element used).

Next, using a known suction filtration apparatus, the particle dispersion that passed through the sieve was repeatedly (5 times) washed with methanol and filtered, and then vacuum dried, giving Polymer Particle B3.

The shapes of the resulting particles were examined with the SEM, whereupon elliptical, needle-shaped or rod-shaped polymer particles were observed here and there, but many nearly spherical particles were also noted. One hundred of the particles were randomly sampled and measured. The $L_{AV}$ was 48.2 μm, and the $P_{AV}$ was 2.1, indicating that the particles had a gentle elliptical shape with a relatively small aspect ratio. Also, extraneous matter and agglomerates that passed through the 200 m sieve were observed to some degree in places, and so the method used here cannot be regarded as a process capable of controlling, at an industrial level, the elliptical, needle-like or rod-like shape.

Comparative Example 4

A suspension was prepared by charging the compounds shown below all at once into a 2,000 mL flask, and stirring at 1,000 rpm with a dispersion mixer stirring element. The suspension was set to an oil bath temperature of 80° C. and heated and stirred for 8 hours under a stream of nitrogen, giving a polymethyl methacrylate polymer particle dispersion.

| | |
|---|---|
| Water | 1,386.5 g |
| Methyl methacrylate | 173.4 g |
| Lauryl peroxide | 8.6 g |
| Polyvinyl pyrrolidone (K-30) | 17.3 g |

The resulting particle dispersion was passed through a 200 m sieve and transferred to a separate 3,000 mL flask, and the flask and stirring element were checked for deposits. Masses of agglomerate from precipitated polymer were observed to some degree on the inner periphery of flask and on the stirring element.

Next, centrifugal separation of the particle dispersion that passed through the sieve was repeated five times, and classifying and washing operations were carried out, giving spherical polymer particles B4 of polymethyl methacrylate alone having an average particle size of 5 μm.

The shapes of the resulting particles were examined with the SEM. The particles were found to be spherical polymer particles having a mean particle size of 5 km.

The MV, $L_{AV}$, $D_{AV}$, $P_{AV}$, particle ingredients and shape for the particles obtained in Working Examples 1 to 5 and Comparative Examples 1 to 4 are shown below in Table 1. In addition, the agglomerate ratios obtained in Working Examples 1 to 5 and Comparative Examples 1 to 4 are shown below in Table 2.

TABLE 1

| | | Polymer particle | MV (μm) | $L_{AV}$ (μm) | $D_{AV}$ (μm) | $P_{AV}$ | Main shape | Extraneous matter in particles | Extraneous matter in synthesis vessel |
|---|---|---|---|---|---|---|---|---|---|
| Working Example | 1 | A1 | 6.7 | 19.1 | 3.0 | 6.8 | elliptical/needle-shaped | substantially none | substantially liquid residues only |
| | 2 | A2 | 9.8 | 23.5 | 3.8 | 7.4 | elliptical/needle-shaped | substantially none | substantially liquid residues only |
| | 3 | A3 | 6.5 | 17.8 | 2.5 | 5.9 | elliptical/needle-shaped | substantially none | substantially liquid residues only |
| | 4 | A4 | 10.5 | 29.4 | 3.3 | 8.4 | elliptical/needle-shaped | substantially none | substantially liquid residues only |
| | 5 | A5 | 16.8 | 51.2 | 5.2 | 10.2 | elliptical/needle-shaped | substantially none | substantially liquid residues only |
| Comparative Example | 1 | B1 | 13.4 | 31.2 | 4.2 | 6.9 | elliptical/needle-shaped | agglomerates/mutually sticking particles | agglomerates |
| | 2 | B2 | 12.1 | 22.7 | 3.6 | 6.2 | elliptical/needle-shaped | agglomerates/mutually sticking particles | agglomerates |
| | 3 | B3 | 21.8 | 48.2 | 20.1 | 2.1 | elliptical/spherical | agglomerates/mutually sticking particles | agglomerates |
| | 4 | B4 | 5.0 | — | — | 1 | spherical | substantially none | agglomerates |

TABLE 2

|  | | Polymer particle | Constituents | Total weight of constituents (g) | Agglomerate 1 (g) | Agglomerate 2 (g) | Agglomerate ratio (%) |
|---|---|---|---|---|---|---|---|
| Working Example | 1 | A1 | methyl methacrylate | 288.0 | 0.9 | 1.5 | 0.8 |
|  | 2 | A2 | methyl methacrylate | 288.0 | 0.8 | 2.1 | 1.0 |
|  | 3 | A3 | methyl methacrylate | 288.0 | 0.9 | 1.0 | 0.7 |
|  | 4 | A4 | styrene sodium p-styrenesulfonate | 300.0 | 1.7 | 1.6 | 1.1 |
|  | 5 | A5 | styrene 2-hydroxyethyl methacrylate | 200.0 | 1.0 | 1.5 | 1.3 |
| Comparative Example | 1 | B1 | methyl methacrylate | 160.0 | 15.9 | 23.8 | 24.8 |
|  | 2 | B2 | styrene sodium p-styrenesulfonate | 300.0 | 22.8 | 37.3 | 20.0 |
|  | 3 | B3 | methyl methacrylate | 288.0 | 13.9 | 29.4 | 15.0 |
|  | 4 | B4 | methyl methacrylate | — | — | agglomerates present | — |

The results confirmed that the production method of the invention is an efficient process that results in little agglomerate.

Working Example 6

A synthesis solution was prepared by charging the compounds shown below all at once into a 2,000 mL flask. The solution was then stirred at room temperature for one hour. The liquid phase was in a state where an aqueous phase portion, an emulsified phase portion and an oil phase portion are intermingled. The pH of the synthesis solution was measured and found to be 7. Next, under a stream of nitrogen, the solution was set to an oil bath temperature of 80° C. and heating and stirring (400 rpm) were begun. After 8 hours of heating and stirring (400 rpm), a methyl methacrylate-ethylene glycol dimethacrylate copolymer particle dispersion was obtained. When the internal temperature reached 40° C. during this step, 1 mol/L hydrochloric acid was added dropwise to the synthesis solution for 15 minutes as a pH adjustor until the pH became 1. The pH at the time of reaction completion was also 1.

| | |
|---|---|
| Water | 1,252.5 g |
| Methanol | 65.9 g |
| Polypropylene glycol (#3000) | 9.0 g |
| Polyvinyl pyrrolidone (K-15) | 32.0 g |
| Sucrose ester of lauric acid | 8.5 g |
| Azobisisobutyronitrile (AIBN) | 30.0 g |
| Methyl methacrylate | 228.3 g |
| Ethylene glycol dimethacrylate | 4.4 g |

The resulting particle dispersion was passed through a 200 μm sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with methanol and filtered, and then vacuum dried, giving Polymer Particle A6. The makeup (molar ratio) of the recurring units in Polymer Particle A6 was methyl methacrylate:ethylene glycol dimethacrylate=99:1.

One hundred of the resulting particles were randomly sampled and their shapes examined with the SEM. The particles were found to be elliptical, needle-shaped or rod-shaped polymer particles. The $L_{AV}$ was 22.4 μm, and the $P_{AV}$ was 6.4.

The particles were checked for extraneous matter, but substantially no deformed matter such as agglomerates or mutually sticking particles was observed.

Working Example 7

(First Step)

A synthesis solution was prepared by charging the compounds shown below all at once into a 2,000 mL flask. The solution was then stirred at room temperature for one hour. The liquid phase was in a state where an aqueous phase portion, an emulsified phase portion and an oil phase portion are intermingled. The pH of the synthesis solution was measured and found to be 6. Next, under a stream of nitrogen, the solution was set to an oil bath temperature of 80° C. and heating and stirring (400 rpm) were begun. After 8 hours of heating and stirring (400 rpm), a styrene-methacrylic acid copolymer particle dispersion was obtained. When the internal temperature reached 40° C. during this step, 1 mol/L hydrochloric acid was added dropwise to the synthesis solution for 15 minutes as a pH adjustor until the pH became 2. The pH at the time of reaction completion was also 2.

| | |
|---|---|
| Water | 1,136.0 g |
| Methanol | 284.0 g |
| Polypropylene glycol (#3000) | 24.0 g |
| Polyvinyl pyrrolidone (K-15) | 8.0 g |
| Polyethylene glycol (PEG 20000) | 4.0 g |
| Azobisisobutyronitrile (AIBN) | 24.0 g |
| Styrene | 240.0 g |
| Methacrylic acid | 60.0 g |

The resulting particle dispersion was passed through a 200 m sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with a mixed solution of methanol and water (weight ratio=7:3) and filtered, and then vacuum dried, giving Polymer Particle A7. The makeup (molar ratio) of the recurring units in Polymer Particle A7 was styrene:methacrylic acid=77:23.

One hundred of the resulting particles were randomly sampled and their shapes examined with the SEM. The particles were found to be elliptical, needle-shaped or rod-shaped polymer particles. The $L_{AV}$ was 15.2 µm, and the $P_{AV}$ was 5.1.

The particles were checked for extraneous matter, but substantially no deformed matter such as agglomerates or mutually sticking particles was observed.

(Second Step)

Next, an epoxy-containing particle dispersion was prepared by charging the mixture in the proportions shown below all at once into a 300 mL flask, carrying out dispersion at room temperature for 1 hour with a disperser, and subsequently adding 0.1 g of tributylamine as a catalyst and carrying out about 8 hours of heating at an oil bath temperature of 70° C. under a stream of nitrogen.

| Particles obtained in first step | 10.0 g |
|---|---|
| Denacol EX-1610 | 14.8 g |
| Methanol | 41.4 g |
| Water | 57.8 g |

[Denacol EX-1610: an epoxy compound produced by Nagase ChemteX Corporation; epoxy equivalent weight, 170]

Next, using a known suction filtration apparatus, the particle dispersion was repeatedly (5 times) washed with a mixed solution of methanol and water (weight ratio=7:3) and filtered, and then vacuum dried, giving Polymer Particle A8.

A portion of the resulting particles was measured with a Fourier transform infrared spectrophotometer (FT-IR8200PC, from Shimadzu Corporation). An absorption peak attributable to epoxy groups was confirmed at a wave number of about 910 ($cm^{-1}$).

One hundred of the resulting particles were randomly sampled and their shapes examined with the SEM. The particles were found to be elliptical, needle-shaped or rod-shaped polymer particles. The $L_{AV}$ was 16.5 µm, and the $P_{AV}$ was 5.3.

The particles were checked for extraneous matter, but substantially no deformed matter such as agglomerates or mutually sticking particles was observed.

Working Example 8

Aside from changing the azobisisobutyronitrile to 21.0 g of ammonium persulfate and changing the stirring speed to 250 rpm, a methyl methacrylate-ethylene glycol dimethacrylate copolymer particle dispersion was obtained in the same way as in Working Example 6. The pH before the start of heating was 7, the pH two hours after the start of heating was 2, and the pH at the time of reaction completion was 1.

The resulting particle dispersion was passed through a 200 m sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with methanol and filtered, and then vacuum dried, giving Polymer Particle A9.

One hundred of the resulting particles were randomly sampled and their shapes examined with the SEM. The particles were found to be elliptical, needle-shaped or rod-shaped polymer particles. The $L_{AV}$ was 21.1 µm, and the $P_{AV}$ was 2.0.

The particles were checked for extraneous matter, but substantially no deformed matter such as agglomerates or mutually sticking particles was observed.

Working Example 9

Aside from changing the polyvinyl pyrrolidone (K-15) in Working Example 6 to 20.0 g, a methyl methacrylate-ethylene glycol dimethacrylate copolymer particle dispersion was obtained in the same way as in Working Example 6. When the internal temperature reached 40° C. during this step, 1 mol/L hydrochloric acid was added dropwise to the synthesis solution for 15 minutes as a pH adjustor until the pH became 1. The pH at the time of reaction completion was also 1.

The resulting particle dispersion was passed through a 200 m sieve and transferred to a separate 3,000 mL flask. Agglomerates 1 and 2 were collected in the same way as in Working Example 1 (the flask and stirring element used were clean, with substantially no deposits observable thereon).

Next, using a known suction filtration apparatus, the particle dispersion that passed through the sieve was repeatedly (5 times) washed with methanol and filtered, and then vacuum dried, giving Polymer Particle A10.

One hundred of the resulting particles were randomly sampled and their shapes examined with the SEM. The particles were found to be elliptical, needle-shaped or rod-shaped polymer particles. The $L_{AV}$ was 56.4 µm, and the $P_{AV}$ was 12.4.

The particles were checked for extraneous matter, but substantially no deformed matter such as agglomerates or mutually sticking particles was observed.

Comparative Example 5

Aside from not carrying out pH adjustment, a methyl methacrylate-ethylene glycol dimethacrylate copolymer particle dispersion was obtained in the same way as in Working Example 6. The pH of the synthesis solution before the start of heating was 7, and the pH two hours after the start of the reaction was also 7.

The resulting particle dispersion was passed through a 200 m sieve and transferred to a separate 3,000 mL flask. Agglomerates 1 and 2 were collected in the same way as in Working Example 1 (masses of agglomerate from precipitated polymer were observed on the inner periphery of the flask and on the stirring element).

Next, using a known suction filtration apparatus, the particle dispersion that passed through the sieve was repeatedly (5 times) washed with methanol and filtered, and then vacuum dried, giving Polymer Particle B5.

The shapes of the resulting particles were examined with the SEM, whereupon elliptical, needle-shaped or rod-shaped polymer particles were observed here and there, but many nearly spherical particles were also noted. One hundred of the particles were randomly sampled and measured. The $L_{AV}$ was 22.1 µm, and the $P_{AV}$ was 1.4, indicating that the particles had a gentle elliptical shape with a relatively small aspect ratio. Also, large numbers of agglomerates and extraneous matter that passed through the 200 m sieve were observed in places, and so the method used here cannot be regarded as a process capable of stably and efficiently producing elliptical, needle-shaped or rod-shaped particles.

The MV, $L_{AV}$, $D_{AV}$, $P_{AV}$ particle ingredients and shape for the particles obtained in Working Examples 6 to 9 and Comparative Example 5 are shown below in Table 3. In addition, the agglomerate ratios obtained in Working Examples 6 to 9 and Comparative Example 5 are shown below in Table 4.

TABLE 3

|  | | Polymer particle | MV (μm) | $L_{AV}$ (μm) | $D_{AV}$ (μm) | $P_{AV}$ | Main shape | Extraneous matter in particles | Extraneous matter in synthesis vessel |
|---|---|---|---|---|---|---|---|---|---|
| Working Example | 6 | A6 | 8.9 | 22.4 | 3.6 | 6.4 | elliptical/needle-shaped | substantially none | substantially liquid residues only |
|  | 7 | A7 | 6.1 | 15.2 | 2.2 | 5.1 | elliptical/needle-shaped | substantially none | substantially liquid residues only |
|  |  | A8 | 6.2 | 16.5 | 2.4 | 5.3 | elliptical/needle-shaped | substantially none | substantially liquid residues only |
|  | 8 | A9 | 11.6 | 21.1 | 9.8 | 2.0 | elliptical/needle-shaped | substantially none | substantially liquid residues only |
|  | 9 | A10 | 10.1 | 56.4 | 3.8 | 12.4 | elliptical/needle-shaped | substantially none | substantially liquid residues only |
| Comparative Example | 5 | B5 | 9.8 | 22.1 | 6.2 | 1.4 | elliptical/spherical | agglomerates/mutually sticking particles | agglomerates |

TABLE 4

|  | | Polymer particle | Constituents | Total weight of constituents (g) | Agglomerate 1 (g) | Agglomerate 2 (g) | Agglomerate ratio (%) |
|---|---|---|---|---|---|---|---|
| Working Example | 6 | A6 | methyl methacrylate ethylene glycol dimethacrylate | 232.7 | 1.0 | 1.0 | 0.9 |
|  | 7 | A7 | styrene methacrylic acid | 300.0 | 1.2 | 2.3 | 1.2 |
|  |  | A8 | styrene methacrylic acid epoxy compound | — | — | — | no agglomerates |
|  | 8 | A9 | methyl methacrylate ethylene glycol dimethacrylate | 232.7 | 1.1 | 1.0 | 0.9 |
|  | 9 | A10 | methyl methacrylate ethylene glycol dimethacrylate | 232.7 | 1.4 | 1.8 | 1.4 |
| Comparative Example | 5 | B5 | methyl methacrylate ethylene glycol dimethacrylate | 232.7 | 32.4 | 48.6 | 34.8 |

[Confirmation of Chemical Resistance Due to Crosslinking]

One gram of the particles obtained in Working Example 6, the particles obtained in the second step of Working Example 7, the particles obtained in Working Example 8, the particles obtained in Working Example 9 or the particles obtained in Comparative Example 1 was placed, together with 100 mL of the solvent indicated in Table 5 below, in a 300 mL flask and stirred for 30 minutes at room temperature, following which the dispersed state of the particles was visually checked in order to ascertain the chemical resistance. In addition, the shape of the particles was checked by SEM. The results of these evaluations are shown in Table 5.

TABLE 5

| Solvent | | | Water | | Methanol | | Ethanol | | Ethyl acetate | | Dimethylformamide | |
|---|---|---|---|---|---|---|---|---|---|---|---|---|
| | | | Visual | SEM | Visual | SEM | Visual | SEM | Visual | SEM | Visual | SEM |
| Working Example | | 6 | ○ | 1 | ○ | 1 | ○ | 1 | ○ | 1 | ○ | 1 |
| | | 7 | ○ | 1 | ○ | 1 | ○ | 1 | ○ | 1 | ○ | 1 |
| | | 8 | ○ | 1 | ○ | 1 | ○ | 1 | ○ | 1 | ○ | 1 |
| | | 9 | ○ | 1 | ○ | 1 | ○ | 1 | ○ | 1 | ○ | 1 |
| Comparative Example | | 1 | ○ | 1 | ○ | 1 | ○ | 1 | X | 3 | X | 3 |

| Solvent | | | Methyl ethyl ketone | | Dipropylene glycol | | Acetone | | Toluene | |
|---|---|---|---|---|---|---|---|---|---|---|
| | | | Visual | SEM | Visual | SEM | Visual | SEM | Visual | SEM |
| Working Example | | 6 | ○ | 1 | ○ | 1 | ○ | 1 | ○ | 1 |
| | | 7 | ○ | 1 | ○ | 1 | ○ | 1 | ○ | 1 |
| | | 8 | ○ | 1 | ○ | 1 | ○ | 1 | ○ | 1 |
| | | 9 | ○ | 1 | ○ | 1 | ○ | 1 | ○ | 1 |

TABLE 5-continued

| Comparative Example | 1 | X | 3 | Δ | 2 | X | 3 | X | 3 |
|---|---|---|---|---|---|---|---|---|---|

○: Dispersed
Δ: Partially dispersed
X: Dissolved
1: Shapes are those of prepared particles
2: Some deformation
3: Shapes of prepared particles absent As shown in Table 5, the particles obtained in Working Example 6, the particles obtained in the second step of Working Example 7, and the particles obtained in Working Examples 8 and 9, because they are crosslinked, were all confirmed to be particles having a high chemical resistance.

Therefore, these production methods were confirmed to be processes that stably and efficiently obtain elliptical, needle-shaped or rod-shaped crosslinked polymer particles.

Consecutive Synthesis

Working Example 10

Particle synthesis was carried out in the same way as in Working Example 1, giving polymethyl methacrylate Particle Dispersion C1. The resulting particle dispersion was passed through a 200 m sieve and transferred to a separate 3,000 mL flask, following which the ingredients mentioned in Working Example 1 were again charged into the flask used for synthesis, and synthesis was consecutively carried out in the same way as in Working Example 1, thereby giving polymethyl methacrylate Particle Dispersion C2.

The resulting Particle Dispersion C2 was passed through a 200 m sieve and transferred to a separate 3,000 mL flask, and agglomerates remaining on the sieve were collected as Agglomerate 1 following treatment as described above. The polymer component (agglomerate) adhering to the interior of the synthesis vessel (the flask and stirring element) was scraped off into the vessel being used and collected as Agglomerate 2 following treatment as described above (the flask and stirring element used were clean, with substantially no deposits observable thereon).

Next, using a known suction filtration apparatus, Particle Dispersion C1 and Particle Dispersion C2 were repeatedly (5 times) washed with methanol and filtered, and then vacuum dried, giving Polymer Particles CA1 and CA2.

One hundred of the resulting particles were randomly sampled and their shapes examined with the SEM. Polymer Particles CA1 were elliptical, needle-shaped or rod-shaped polymer particles. The $L_{AV}$ was 19.8 μm, and the $P_{AV}$ was 6.7.

Polymer Particles CA2 were also elliptical, needle-shaped or rod-shaped polymer particles. The $L_{AV}$ was 20.2 μm, and the $P_{AV}$ was 6.9. This demonstrated that substantially similar elliptical, needle-shaped or rod-shaped polymer particles can be obtained even when consecutive synthesis is carried out. Polymer Particles CA1 and Polymer Particles CA2 were checked for extraneous matter, but substantially no deformed matter such as agglomerates or mutually sticking particles was observed.

Comparative Example 6

Particle synthesis was carried out in the same way as in Comparative Example 1, giving polymethyl methacrylate Particle Dispersion C3. The resulting particle dispersion was passed through a 200 m sieve and transferred to a separate 3,000 mL flask, following which the flask used in synthesis was used to carry out consecutive synthesis in the same way, thereby giving polymethyl methacrylate Particle Dispersion C4.

Particle Dispersion C4 was passed through a 200 m sieve and transferred to a separate 3,000 mL flask, and agglomerates remaining on the sieve were collected as Agglomerate 1 following treatment as described above. The polymer component (agglomerate) adhering to the interior of the synthesis vessel (the flask and stirring element) was scraped off into the vessel being used and collected as Agglomerate 2 following treatment as described above (the flask and stirring element used were clean, with substantially no deposits observable thereon).

Next, using a known suction filtration apparatus, Particle Dispersion C3 and Particle Dispersion C4 were repeatedly (5 times) washed with methanol and filtered, and then vacuum dried, giving Polymer Particles CB1 and CB2.

When the shapes of the resulting particles were examined with the SEM, elliptical, needle-shaped or rod-shaped polymer particles were sporadically observed in Polymer Particle CB1. One hundred particles were randomly sampled; the $L_A V$ was 32.8 μm, and the $P_{AV}$ was 6.8. However, large numbers of agglomerates and extraneous matter that passed through the 200 m sieve were observed in places.

In Polymer Particle CB2, elliptical, needle-shaped or rod-shaped polymer particles were obtained, but were very few in number; the majority of the particles were spherical particles or were extraneous matter or agglomerates that passed through the sieve.

The MV, $L_{AV}$, $D_{AV}$, $P_{AV}$ particle ingredients and shape for the particles obtained in Working Example 10 and Comparative Example 6 are shown below in Table 6. In addition, the agglomerate ratios obtained in Working Example 10 and Comparative Example 6 are shown in Table 7.

TABLE 6

| | Polymer particle | MV (μm) | $L_{AV}$ (μm) | $D_{AV}$ (μm) | $P_{AV}$ | Main shape | Extraneous matter in particles | Extraneous matter in synthesis vessel |
|---|---|---|---|---|---|---|---|---|
| Working Example 10 | CA1 | 6.6 | 19.8 | 2.9 | 6.7 | elliptical/needle-shaped | substantially none | substantially liquid residues only |
| | CA2 | 6.8 | 20.2 | 3.1 | 6.9 | elliptical/needle-shaped | substantially none | substantially liquid residues only |

TABLE 6-continued

| | Polymer particle | MV (μm) | $L_{AV}$ (μm) | $D_{AV}$ (μm) | $P_{AV}$ | Main shape | Extraneous matter in particles | Extraneous matter in synthesis vessel |
|---|---|---|---|---|---|---|---|---|
| Comparative Example 6 | CB1 | 13.7 | 32.8 | 4.3 | 6.8 | elliptical/ needle-shaped | agglomerates/ mutually sticking particles | agglomerates |
| | CB2 | 19.8 | 25.1 | 18.1 | 1.3 | spherical/ elliptical | agglomerates/ mutually sticking particles | agglomerates |

TABLE 7

| | Polymer particle | Constituents | Total weight of constituents (g) | Agglomerate 1 (g) | Agglomerate 2 (g) | Agglomerate ratio (%) |
|---|---|---|---|---|---|---|
| Working Example 10 | CA1 | methyl methacrylate | 288.0 | — | — | — |
| | CA2 | methyl methacrylate | 288.0 | 1.4 | 1.3 | 0.9 |
| Comparative Example 6 | CB1 | methyl methacrylate | 160.0 | — | — | — |
| | CB2 | methyl methacrylate | 160.0 | 35.2 | 28.8 | 40.0 |

The results in Tables 6 and 7 show that, with the production method of the invention, because there are substantially no residues adhering to the stirring element and vessel interior following synthesis, consecutive synthesis is possible. Hence, even in consecutive synthesis, the method of the invention is excellent for stably and efficiently producing elliptical, needle-shaped or rod-shaped polymer particles. These findings thus confirm that the production method of the invention is an efficient process that is capable of mass production.

Evaluation of Properties

Preparation and Evaluation of Optical Measurement Sheets

Working Example 11, Comparative Examples 7 and 8

Compositions were prepared by mixing Polymer Particle A1 (Working Example 11), Polymer Particle B1 (Comparative Example 7) or Polymer Particle B4 (Comparative Example 8) with a binder resin (a PVA resin from Kuraray Co., Ltd.) and purified water in the proportions shown in Table 8 below. The compositions were then coated onto one side of a 100 μm thick PET film (E-5000, from Toyobo Co., Ltd.) using a commercial bar coater. After coating, a drying oven was set to 50° C. and forced hot-air drying was carried out for 20 minutes, thereby producing Optical Sheets 1 to 3 in such a way that the thickness of the applied layer became 40 μm.

TABLE 8

| | Optical sheet | Polymer particles (g) A1 | Polymer particles (g) B1 | Polymer particles (g) B4 | Binder resin (g) | Purified water (g) | Main shape | Remarks |
|---|---|---|---|---|---|---|---|---|
| Working Example 11 | 1 | 15.0 | — | — | 35.0 | 75.0 | elliptical/ needle-shaped | |
| Comparative Example 7 | 2 | — | 15.0 | — | 35.0 | 75.0 | elliptical/ needle-shaped | agglomerates present |
| Comparative Example 8 | 3 | — | — | 15.0 | 35.0 | 75.0 | spherical | |

Note:
In each case, the particle constituent was methyl methacrylate

Evaluation Test 1

Transmitted light analysis at wavelengths of 360 nm, 500 nm, 600 nm and 700 nm was carried out on Optical Sheets 1 to 4 using a UV-visible spectrophotometer (UV-2450, from JASCO Corporation). The results are shown in Table 9.

TABLE 9

| | Optical sheet | Transmittance (%) | | | | Particle shape |
| --- | --- | --- | --- | --- | --- | --- |
| | | 360 nm | 500 nm | 600 nm | 700 nm | |
| Working Example 11 | 1 | 9.6 | 16.5 | 25.4 | 32.5 | elliptical/needle-shaped |
| Comparative Example 7 | 2 | 19.3 | 29.5 | 39.3 | 48.6 | elliptical/needle-shaped + agglomerates |
| Comparative Example 8 | 3 | 31.4 | 42.8 | 54.2 | 63.4 | spherical |

From the results of transmitted light analysis and the fact that the transmitted light decreases in Working Example 11 at the optical sheet, it was confirmed that the light-scattering effect distinctive to elliptical shapes is clearly obtained. Also, the fact that the light-scattering effect is high in the UV-to-visible light spectrum demonstrated that the hiding power is also high.

Moreover, in Comparative Example 7, although the light-diffusing effects and hiding power of elliptical shapes can be obtained relative to the spherical particles in Comparative Example 8, these effects were confirmed to be diminished relative to Working Example 11 on account of the presence of agglomerates.

Evaluation of Reflected Light Scattering Ability

Evaluation Test 2

Working Example 12, Comparative Examples 9 and 10

Test sheets were prepared by uniformly applying 0.24 mg/cm$^2$ of Polymer Particle A1 (Working Example 12), Polymer Particle B1 (Comparative Example 9) or Polymer Particle B4 (Comparative Example 10) onto black synthetic leather (5 cm×8 cm) while patting with a cosmetic powder puff. Next, using an automated goniophotometer (GP-200, from Murakami Color Research Laboratory Co., Ltd.), a fixed amount of light was irradiated onto the test sheet at an incident angle of 45° and the light scattering distribution of the reflected light was measured. The results are shown in FIG. 3.

It was confirmed from FIG. 3 that a reflected light-scattering effect distinctive to particles of elliptical shape can be obtained in Working Example 12. Moreover, because the scattering effect is high even in the UV-to-visible light spectrum, the hiding power was confirmed to be high.

In addition, although the light-scattering effects of particles of elliptical shape are obtained in Comparative Example 9 relative to the spherical particles in Comparative Example 10, on account of the presence of agglomerates, these effects were found to be diminished compared with Working Example 12.

Sensory Tests and Evaluation of Adhesion

Evaluation Test 3

Working Example 13, Comparative Examples 11 and 12

Polymer Particle A1 (Working Example 13), Polymer Particle B1 (Comparative Example 11) and Polymer Particle B4 (Comparative Example 12) were evaluated by the methods shown below. The results are shown in Table 10.

Evaluated Qualities
  Feel: The tactile feel of each type of particle when spread over the skin was evaluated.
  Slip characteristics: The slip characteristics were evaluated by placing 1 g of each type of particle on black synthetic leather, and measuring the length when spread with a finger.
  Particle adhesion: One gram of each type of particle was placed on black synthetic leather and uniformly spread with a powder puff, following which the leather was struck three times and the amount of particles remaining was examined with a digital microscope (VHX200, from Keyence Corporation).

Evaluation Criteria
  Feel:
    O: Tactile sensation is apparent, with application to skin being pleasant
    Δ: Tactile sensation is apparent, but ordinary
    X: Tactile sensation is apparent, but unpleasant
  Slip characteristics:
    O: Particles spread well
    Δ: Ordinary
    X: Particles do not spread
  Particle adhesion:
    O: Adhered state is substantially maintained
    Δ: Local peeling observed here and there
    X: Most of the applied particles peeled and fell off

TABLE 10

| | Particle | Feel | Slip characteristics | Particle adhesion | Major shape |
| --- | --- | --- | --- | --- | --- |
| Working Example 13 | A1 | O | O | O | elliptical/needle-shaped |
| Comparative Example 11 | B1 | Δ | Δ | Δ | elliptical/needle-shaped + agglomerates |
| Comparative Example 12 | B4 | Δ | O | X | spherical |

It was confirmed from these results that characteristics distinctive to an elliptical shape are exhibited in Working Example 13. The characteristics of an elliptical shape are apparent in Comparative Example 11 as well, but owing to the presence of agglomerates, those effects tended to diminish. The spherical particles in Comparative Example 12 had a poor adhesion because of their spherical shape.

Preparation and Evaluation of Cosmetics

Evaluation Test 4

Foundations 1 to 3 (powders) were prepared according to the compositions shown in Table 11.

TABLE 11

| Compositions | Weight (g) | | |
|---|---|---|---|
| | Foundation 1 | Foundation 2 | Foundation 3 |
| Red iron oxide | 0.4 | 0.4 | 0.4 |
| Yellow iron oxide | 1.0 | 1.0 | 1.0 |
| Black iron oxide | 0.2 | 0.2 | 0.2 |
| Titanium oxide | 7.0 | 7.0 | 7.0 |
| Zinc oxide | 3.0 | 3.0 | 3.0 |
| Silicone-treated large particle-size titanium oxide | 3.0 | 3.0 | 3.0 |
| Lauroyl lysine powder | 14.0 | 14.0 | 14.0 |
| Titanium-mica powder | 4.0 | 4.0 | 4.0 |
| Talc | 35.97 | 35.97 | 35.97 |
| Methyl phenyl polysiloxane | 2.0 | 2.0 | 2.0 |
| Crystalline cellulose | 5.0 | 5.0 | 5.0 |
| Cornstarch | 10.0 | 10.0 | 10.0 |
| Methyl paraben | 0.1 | 0.1 | 0.1 |
| Sodium dehydroacetate | 0.1 | 0.1 | 0.1 |
| Liquid paraffin | 1.5 | 1.5 | 1.5 |
| Butylene glycol | 0.5 | 0.5 | 0.5 |
| Job's tears extract | 0.1 | 0.1 | 0.1 |
| Ginseng root extract | 0.1 | 0.1 | 0.1 |
| Ubiquinone | 0.03 | 0.03 | 0.03 |
| Polymer particle A1 (Working Example 1) | 12.0 | — | — |
| Polymer particle B1 (Comparative Example 1) | — | 12.0 | — |
| Polymer particle B4 (Comparative Example 4) | — | — | 12.0 |

Ten people were selected as panelists, and the following five qualities were evaluated overall for Foundations 1, 2 and 3: "adhesion to skin," "sense of fit when applied," "feel during use," "soft focus effect" and "durability of cosmetic effect (4 hours)," based on which the acceptability of the cosmetic formulation was assessed.

A: Foundation 1 was best
B: Foundation 2 was best
C: Foundation 3 was best
D: They were all the same As a result, the assessments by the panelists were as follows:

A: 6 panelists
B: 3 panelists
C: 1 panelist
D: 0 panelists.

Moreover, many of the panelists thought that Foundation 1 was particularly outstanding with respect to the "adhesion to skin," "soft focus effect" and "durability of cosmetic effect (4 hours)." Many of the panelists thought that Foundation 2 had drawbacks with respect to the "sense of fit when applied" and the "feel during use," presumably on account of the large influence by agglomerates. In addition, many thought that Foundation 3 lacked "adhesion to skin" and "durability of cosmetic effect (4 hours)."

The above results demonstrate that the production method of the invention can stably and efficiently produce elliptical, needle-shaped or rod-shaped polymer particles having little extraneous matter such as agglomerate, and moreover can stably produce crosslinked particles, thus enabling such particles to be utilized in various applications.

Moreover, these evaluation results demonstrate that because the elliptical, needle-shaped or rod-shaped polymer particles obtained by the production method of the invention fully retain the properties inherent to the elliptical, needle-like or rod-like shape, they are expected to be capable of being effectively utilized in applications requiring polymer particles, such as paints, inks, molded or formed articles, cosmetics, light diffusing sheets and other optical materials, and thermally cavitated products having pores.

The invention claimed is:

1. A method for producing elliptical, needle-shaped or rod-shaped polymer particles which satisfy conditions (1) to (3) below:
   (1) a two-dimensional projection obtained by irradiating the particle with light from a direction orthogonal to a long axis of the particle has a length L with an average value $L_{AV}$ of from 0.1 to 80 μm,
   (2) a two-dimensional projection obtained by irradiating the particle with light from a direction orthogonal to a long axis of the particle has a breadth D with an average value $D_{AV}$ of from 0.05 to 40 μm, and
   (3) the aspect ratio L/D calculated from the length L and breadth D has an average value $P_{AV}$ of from 1.5 to 30,
   the method comprising the step of carrying out solution polymerization by heating a synthesis solution containing a mixed solvent of water, a hydrophilic organic solvent and a hydrophobic organic solvent, a high-molecular-weight stabilizer, a polymerization initiator and an unsaturated monomer and, at least after the start of heating, adjusting the pH of the synthesis solution to 5 or less.

2. The method for producing elliptical, needle-shaped or rod-shaped polymer particles of claim 1, wherein the mixing ratio of the water, hydrophilic organic solvent and hydrophobic organic solvent, expressed as a weight ratio, is from 99:0.5:0.5 to 25:55:20.

3. The method for producing elliptical, needle-shaped or rod-shaped polymer particles of claim 1, wherein the hydrophobic organic solvent is a high-molecular-weight compound having a molecular weight of at least 200.

4. The method for producing elliptical, needle-shaped or rod-shaped polymer particles of claim 1, wherein the unsaturated monomer includes at least one monomer selected from the group consisting of styrenic monomers, (meth)acrylic ester monomers, vinyl carboxylate monomers and polyfunctional unsaturated monomers.

5. The method for producing elliptical, needle-shaped or rod-shaped polymer particles of claim 1, wherein the unsaturated monomer contains at least one reactive functional group selected from epoxy, hydroxyl, carboxyl, amino, amide and thiol groups.

* * * * *